(12) United States Patent
Maiefski et al.

(10) Patent No.: US 6,416,718 B1
(45) Date of Patent: Jul. 9, 2002

(54) SAMPLE WASH STATION ASSEMBLY

(75) Inventors: Romaine Maiefski, Ocean Side; Don Wendell, San Diego, both of CA (US)

(73) Assignee: Ontogen Corporation, Carlsbad, CA (US)

( * ) Notice: Subject to any disclaimer, the term of this patent is extended or adjusted under 35 U.S.C. 154(b) by 0 days.

(21) Appl. No.: 09/334,750

(22) Filed: Jun. 16, 1999

Related U.S. Application Data

(62) Division of application No. 09/087,376, filed on May 29, 1998, now Pat. No. 5,976,470.

(51) Int. Cl.[7] .......................... G01N 35/10; G01N 1/14
(52) U.S. Cl. .................... 422/103; 422/65; 422/100; 436/43; 436/174; 436/180; 222/144.5; 222/485
(58) Field of Search ................... 422/63, 68, 68.1, 422/81, 100–104; 436/43, 49, 174, 179, 180; 222/144.5, 137, 330, 485

(56) References Cited

U.S. PATENT DOCUMENTS

| | | | |
|---|---|---|---|
| 3,944,188 A | | 3/1976 | Parker et al. .................. 259/54 |
| 4,054,151 A | | 10/1977 | Parker et al. ................. 137/110 |
| 4,106,911 A | | 8/1978 | Marcelli ....................... 23/259 |
| 5,195,656 A | * | 3/1993 | Briehl et al. .................... 222/1 |
| 5,232,664 A | * | 8/1993 | Krawzak et al. ............... 422/64 |
| 5,525,302 A | | 6/1996 | Astle .......................... 422/100 |
| 5,609,826 A | | 3/1997 | Cargill et al. ................. 422/99 |
| 5,660,792 A | * | 8/1997 | Koike .......................... 422/63 |
| 5,788,927 A | * | 8/1998 | Farrell et al. ................. 422/63 |
| 5,807,523 A | | 9/1998 | Watts et al. ................... 422/64 |
| 5,888,830 A | | 3/1999 | Mohan et al. ............... 436/174 |
| 5,916,524 A | * | 6/1999 | Tisone ......................... 422/100 |

FOREIGN PATENT DOCUMENTS

WO       WO 97/14041       4/1997

* cited by examiner

Primary Examiner—Jill Warden
Assistant Examiner—Kathryn Bex
(74) Attorney, Agent, or Firm—Perkins Coie LLP

(57) ABSTRACT

A wash station assembly and method for washing selected samples in a sample containing assembly. The wash station assembly includes a wash station having a frame and a fluid dispensing assembly connected to the frame. The fluid dispensing assembly has a selector valve that is connectable to a plurality of fluid lines and is adjustable to allow only one of the fluids to pass through the selector valve at a time. An array of syringes is coupled to the selector valve and positioned to receive the fluid passing through the selector valve. Each syringe includes a check valve that prevents backflow of fluid or air into the syringe through the pipetting needles. A distribution manifold is connected to the selector valve and receives the fluid passing through the selector valve. The manifold has a plurality of distribution channels coupled to the syringes, to direct the fluid into the syringes. Each distribution channel has a manifold valve therein that prevents backflow of fluid into the manifold from the syringes. An array of pipetting needles is connected to the syringes and is positioned to direct the fluid into the sample containing assembly for washing the samples. The pipetting needles have a radially directed opening in the distal end to direct the fluid radially away from the needle during the dispensing process. A waste management system is connected to the wash station to automatically separate halogenated waste fluids from non-halogenated waste fluids.

15 Claims, 19 Drawing Sheets

SAMPLE WASH STATION ASSEMBLY

CROSS-REFERENCE TO RELATED APPLICATION

This application is a divisional of pending U.S. patent application Ser. No. 09/087,376, filed May 29, 1998, now U.S. Pat. No. 5,976,470.

TECHNICAL FIELD

The present invention is generally directed to apparatus and methods to aid in the generation of chemical libraries of known compositions and, more particularly, to automated fluid dispensing and distniution assemblies, including wash stations, used during generation of chemical libraries.

BACKGROUND OF THE INVENTION

The relationship between structure and function of molecules is a fundamental issue in the study of biological and other chemistry-based systems. Structure-function relationships are important in understanding, for example, the function of enzymes, cellular communication, and cellular control and feedback mechanisms. Certain macromolecules are known to interact and bind to other molecules having a specific three-dimensional spatial and electronic distribution. Any macromolecule having such specificity can be considered a receptor, whether the macromolecule is an enzyme, a protein, a glycoprotein, an antibody, or an oligonucleotide sequence of DNA, RNA or the like. The various molecules which bind to receptors are known as ligands.

A common way to generate such ligands is to synthesize molecules in a stepwise fashion on solid phase resins. Since the introduction of solid phase synthesis methods for peptides, oligonucleotides and small organic molecules, new methods employing solid phase strategies have been developed that are capable of generating thousands, and in some cases even millions, of individual molecules using automated or manual techniques. These synthesis strategies, which generate families or libraries of molecules, are generally referred to as "combinatorial chemistry" or "combinatorial synthesis" strategies. In the pharmaceutical industry these families or libraries of molecules are often formatted into 96 well plates. This formatting provides a convenient method to screen these molecules to identify novel ligands for biological receptors.

To aid in the generation of combinatorial chemical libraries, scientific instruments have been produced which automatically perform many or all of the chemical steps required to generate such libraries. An example of an automated combinatorial chemical library synthesizer is described in PCT Patent Application No. WO 97/14041, published Apr. 17, 1997, assigned to the assignee of the present invention, and incorporated herein in its entirety by reference. Another example of an automated combinatorial chemical library synthesizer is the Model 396 MPS fully automated multiple peptide synthesizer, manufactured by Advanced ChemTech, Inc. ("ACT") of Louisville, Ky. A further example of an automated combinatorial chemical library synthesizer is described in U.S. Pat. No. 5,609,826, entitled "METHODS AND APPARATUS FOR THE GENERATION OF CHEMICAL LIBRARIES," issued Mar. 11, 1997, assigned to the assignee of the present invention, and incorporated herein in its entirety by reference.

In such automated chemical library synthesizers, many different molecules are synthesized simultaneously on solid supports, with a different molecule or set of molecules being synthesized in each reaction chamber. One set of reagents is added to the solid support before the addition of the next successive set of reagents is added. Thus, each growing molecule or set of molecules is the sized in a stepwise fashion via the addition of sets of input reagents into each reaction chamber.

As is known to those skilled in the art, the process of combinatorial synthesis not only requires the introduction of a series of reagents, but also requires washing, deblocking, capping, and other reaction steps as well. These steps must be performed regardless of the sequence in which the various reagent sets are introduced into the reaction chambers.

In some automated combinatorial chemical library synthesizers, which incorporate pipetting workstations such as the TECAN 5032 (manufactured by TECAN AG, Feldbachstrasse 80, CH-8634 Hombrechtiken, Switzerland), only one or two pipetting needles can be used to introduce the reagents or solvents used in the washing, deblocking, capping, or other commonly performed steps. Since these steps can be performed simultaneously in all of the reaction chambers, the use of only one or two pipetting needles to introduce the appropriate reagents or solvents creates a significant increase in the length of time needed to synthesize a combinatorial chemical library.

Another limiting factor in the time to produce a combinatorial chemical library is the use of an immovable reaction block installed on the operating deck of a pipetting work station. If all the procedural steps for synthesizing a chemical library must take place while the reaction block is located on the operating deck of a pipetting work station, the work station is filly occupied for the duration of the chemical synthesis. This duration may encompass hours or even days for a reaction sequence to be completed. On the other hand, the use of a movable reaction block (such as employed by Cargill and Maiefski in U.S. Pat. No. 5,609,826) allows one to employ a variety of pipetting work stations.

Yet another limiting factor in the time to produce a combinatorial chemical library is the use of a non-standard format reaction block. The use of a reaction block with 96 chambers, which allows one to synthesize combinatorial chemical libraries on 96-well microtiter plate format (with the wells on 9 mm centers), reduces the time involved in pipetting libraries into a standard 96-well format after synthesis. Thus, these libraries can be screened directly against a variety of receptors, without reformatting. For an example of such a reaction block see Cargill and Maiefski in U.S. Pat. No. 5,609,826.

Each pipetting work station may be uniquely tailored to a specific task required in the chemical synthesis (see Cargill and Maiefski in U.S. Pat. No. 5,609,826). The function of each pipetting work station may be to deliver individual reagents or sets of reagents to specific locations in a reaction block. Alternatively, the finction of a pipetting work station may be to deliver an individual reagent or set of reagents to all locations of the reaction block. The function of such work stations may be best tailored to a specific set of pipetting tasks. As is known to those skilled in the art, many chemical steps that require washing, deblocking, capping, etc. are best performed simultaneously, or in other words, in parallel, in a reaction block. Thus the pipetting or delivery of washing solvents, deblocking and capping reagents, or other reagents common to all locations in the reaction block is also best performed in parallel.

The wash station described in WO 97/14041 provides a significantly improved automated wash station that has an array of 96 pipetting needles that simultaneously introduce reagents or solvents into the 96 reaction chambers in the reaction blocks. Accordingly, a synthesizing step of washing, deblocking, capping, or the like of multiple samples is done in parallel, thereby reducing the time and cost of generating a combinatorial chemical library. The synthesizing process, however, still includes time-consuming steps. For example, different reaction blocks having different samples therein often require the use of different solvents during a washing step. Furthermore, changing between solvents for washing, or changing between reagents for deblocking, for example, also includes time-consuming steps. Changing between solvents and recalibrating the wash station to provide the appropriate amount of a selected solvent for each sample can be a difficult and time-consuming process;

Other difficulties experienced by the conventional wash stations include accurately distributing a selected amount of solvent or reagent to all of the needles for simultaneous distribution into the reaction chambers. Failure to use accurate amounts of the solvent or reagent can provide inaccurate results, compromise the synthesizing process, and jeopardize the reliability of the chemical library. Such difficulties are magnified when trying to distribute the selected solvent or reagent to a large number of pipetting needles, such as an array of ninety-six needles.

A further difficulty experienced in synthesizing processes is that the same wash station typically uses a variety of halogenated and non-halogenated solvents. Disposal of the halogenated solvent can be a laborious and costly process, because disposal of the halogenated solvents must be carefully controlled for legal and environmental reasons. Disposal of the non-halogenated solvents, on the other hand, is less rigorous. Accordingly, the waste solvents are separated between halogenated and non-halogenated solvents. The separation process, however, has been a difficult process to effectively perform efficiently and inexpensively. Therefore, there remains a need in the art for an apparatus and method for quickly and efficiently performing certain reaction steps (such as washing, deblocking, capping, etc.) simultaneously and for managing the waste products (such as halogenated and non-halogenated solvents) resulting from the reaction steps.

SUMMARY OF THE INVENTION

The present invention provides a fluid dispensing assembly for dispensing a selected fluid into multiple vessels and methods of dispensing selected fluids or samples that overcome the drawbacks experienced by the prior art and provides further related advantages. In one embodiment of the invention, the fluid dispensing system includes a distribution manifold with a manifold inlet positioned to receive fluid from the fluid source. The distribution manifold has a plurality of distribution channels that are all coupled to the manifold inlet. The distribution channels each have a separate channel outlet through which the fluid can flow. Each distribution channel also has a valve therein to allow the fluid to flow in one direction in the respective distribution channel. An array of fluid dispensers is connected to the distribution manifold. Each fluid dispenser is connected to the channel outlet of a respective distribution channel to receive the fluid passing through the channel outlet. Each fluid dispenser has a valve therein to allow the fluid to flow in one direction out of the respective fluid dispenser.

In another embodiment of the invention the fluid dispensing system is a wash station assembly connectable to a plurality of solvent sources by separate solvent lines. The wash station includes a solvent dispensing assembly connected to a frame, and the solvent dispensing assembly has a selector valve that is connectable to the solvent lines. The selector valve is adjustable between a plurality of positions, and each position allows only one of the solvents to pass through the selector valve at a time.

The selector valve is connected by a distribution manifold to an array of solvent-retaining members, such as syringes or the like, so the solvent passing through the selector valve is distributed to the syringes via the distribution manifold The distribution manifold has a manifold inlet connected to the selector valve and positioned to receive the solvent from the selector valve. The distribution manifold has a plurality of distribution channels that communicate with the manifold inlet, and each distribution channel is connected to a respective one of the syringes. The distribution channels each have an outlet that directs the solvent into the respective syringe. The syringes are connected to an array of distributor members, such as pipetting needles or the like, that receive the solvent dispensed from the syringes. Pipetting needles and syringes are positionable relative to a sample containing assembly, such as a reaction block or the like, to dispense the solvent into samples within the sample containing assembly.

In one embodiment of the invention, the wash station assembly includes a programmable controller that is operatively connected to the selector valve to control the position of the selector valve, and thus control the solvent passing therethrough to the distribution manifold. The selector value also includes a position sensor coupled to the controller so the controller can monitor and identify the selector valve's position, thereby monitoring which solvent is passing through the selector valve.

In one embodiment, the solvent dispensing assembly is movably connected to a distributor support, and the distributor support is movably connected to the frame, so the solvent distributing assembly is movable as a unit laterally and vertically relative to the frame. The solvent dispensing assembly has the array of syringes extending between the distribution manifold and an upper support plate. The upper support plate is movable relative to the distribution manifold between upper and lower positions. The syringes are extended and moved along an aspirating stroke to fill each syringe with a selected amount of the solvent when the upper support plate is moved from the lower position to the upper position. The syringes are compressed and movable through a discharge stroke to discharge the solvent through the respective pipetting needles when the upper support plate is moved from the upper position to the lower position. A check valve is positioned in each distributor channel in the distribution manifold to prevent backflow of the solvent out of the syringe during the syringe's dispensing stroke.

Each syringe receives the solvent from the distribution manifold during the aspirating stroke through an inlet port formed in a syringe connector, which is removably connected to the distribution manifold. The connector also includes an outlet port that directs the solvent out of the syringe into the pipetting needle during the dispensing stroke. A valve, such as a check valve, is positioned in the outlet port to allow the solvent to flow out of the syringe while preventing the solvent or air from entering the syringe through the outlet port during the aspirating stroke. The check valve also prevents solvent from flowing into the distribution manifold from the syringe during the discharge stroke. Accordingly, the solvent has a one-way path into the syringe from the distribution manifold and a one-way path out of the syringe through outlet port and the pipetting needle.

In another embodiment of the invention, the wash station assembly includes a waste management system connected to the wash station to receive waste solvent from the wash station. The waste management system includes a flow control valve that selectively directs the waste solvent to a first or second waste solvent receptacle, depending upon the type of solvent discharged from the wash station. The flow control valve is coupled to the controller, which is connected to the selector valve, and the controller automatically adjusts the flow control valve's position based upon the type of solvent (e.g. a halogenated or non-halogenated solvent) that is passed through the selector valve. Accordingly, the waste management system provides for automated separation of solvents used by the wash station.

The present invention also provides a method for washing a selected sample in a wash station assembly. In one embodiment of the invention, the method includes the steps of passing a plurality of solvents through separate solvent lines to an adjustable selector valve of a wash station assembly, adjusting the selector valve to allow one of the solvents to flow through the selector valve to a distributor manifold, and substantially simultaneously distributing with the distributor manifold a selected amount of the solvent into a plurality of solvent distributing assemblies. The method further includes substantially simultaneously dispensing the solvent from the solvent distributing assemblies into a plurality of sample containers, and washing the samples in the sample containers.

In another embodiment of the invention, the method includes the steps of determining if the solvent is a halogenated or a non-halogenated solvent, removing the solvent from the sample containers, and directing the solvent into a waste line that is connected to a first waste receptacle for halogenated solvents and a second waste receptacle for non-halogenated solvents. The method further includes positioning a flow control valve, which is connected to the waste line, in a first position when the solvent is a halogenated solvent to direct the halogenated solvent to the first receptacle. The method further includes positioning the flow control valve in a second position when the solvent is a non-halogenated solvent to direct the solvent to the second waste receptacle.

A further embodiment of the method includes the steps of adjusting the selector valve from a first position to a second position to allow only a second one of the solvents to pass through the selector valve, with the other solvents being blocked from passing through the selector valve. The method further includes distributing the second solvent into the solvent distributing assemblies, dispensing the second solvent into sample containers, and washing samples in the sample containers.

DETAILED DESCRIPTION OF THE INVENTION

The structure and function of exemplary embodiments of the present invention can best be understood by reference to the drawings. When the same reference numbers appear in multiple figures, the reference numbers refer to the same or corresponding structure in those figures.

Figure 1:
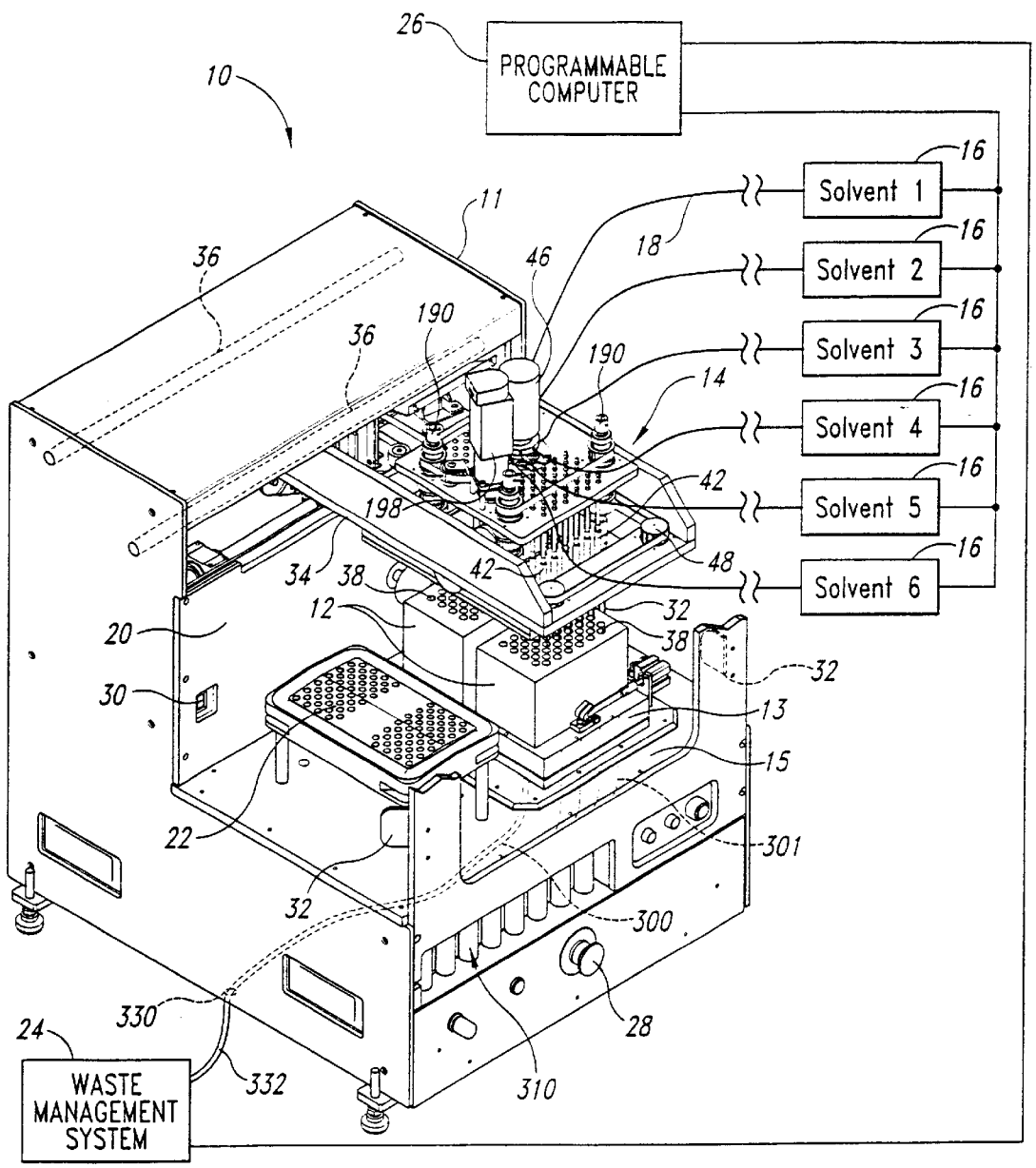
FIG. 1 is a partially fragmented top isometric view of a wash station assembly with a wash station, solvent sources, a programmable controller, and a waste management system in accordance with an embodiment of the present invention, wherein a front portion of the frame is not shown for purposes of clarity.

A wash station assembly 10 in accordance with an exemplary embodiment of the present invention is shown in FIG. 1. The wash station assembly 10 includes a wash station 11 that is operatively connected to a programmable controller 26, such as a computer or the like, for automated control during a synthesizing process. The wash station 11 is connected to six pressurized solvent sources 16 by six solvent lines 18. The wash station 11 is adapted to select one of the six solvents, such as a halogenated solvent or non-halogenated solvent, for use in washing solid phase samples. The wash station 11 is also connected to a waste management system 24 that receives, separates, and contains waste solvent after the washing process.

The wash station 11 has a docking station 13 mounted to a platform 15, and the docking station removably receives two reaction blocks 12 that contain the samples. The docking station 13 used in the exemplary embodiment is discussed and described in the co-pending U.S. Patent Application No. (Pending), assigned to the assignee of the present invention and entitled "REACTION BLOCK DOCKING STATION," filed Mar. 6, 1998, which is hereby incorporated in its entirety by reference thereto. The reaction blocks 12 used in the exemplary embodiment are conventional reaction blocks as discussed and described in U.S. Pat. No. 5,609,826, assigned to the assignee of the present invention. The reaction blocks 12 contain selected samples in a plurality of reaction chambers 38 that receive the selected solvent during a wash process. The wash station 11 also removably receives a plurality of conventional rinse tubes 22 on the platform 15 adjacent to the reaction blocks 12 for use during the needle rinse process.

As best seen in FIG. 1, the wash station 11 has a solvent dispensing assembly 14 positioned above the platform 15 and movably mounted on a frame 20. The dispensing assembly 14 is positionable over the reaction blocks 12 and has an array of pipetting needles 32 that dispense the selected solvent into the reaction blocks. The dispensing assembly 14 is also positionable over the rinse tubes 22 and movable to rinse the pipetting needles 32.

After the solvent is dispensed into the reaction blocks 12, the reaction blocks can be shaken by a vortexing shaker that is coupled to the docking station 13 so as to vortex the solvent or other liquid in the reaction chambers for a selected period of time. The wash station 11 then drains the solvent from the reaction blocks by applying a positive pressure or a partial vacuum to the reaction blocks. The waste solvent flows from the wash station 11 into the waste management system 24. The waste management system 24 is operatively connected to the controller 26, which configures the waste management system to direct the waste solvent into a selected waste receptacle, depending upon the type of solvent (e.g., halogenated or non-halogenated) discharged from the wash station 11.

Wash Station

As best seen in FIG. 1, the wash station 11 includes a pair of support rails 36 attached to the frame 20, and a distributor support 34 is slidably mounted on the support rails for lateral movement relative to the frame. The distributor support 34 supports the dispensing assembly 14 above the wash station's platform 15. Accordingly, the distributor support 34 and the dispensing assembly 14 are laterally movable as a unit above the platform 15.

Figure 2:
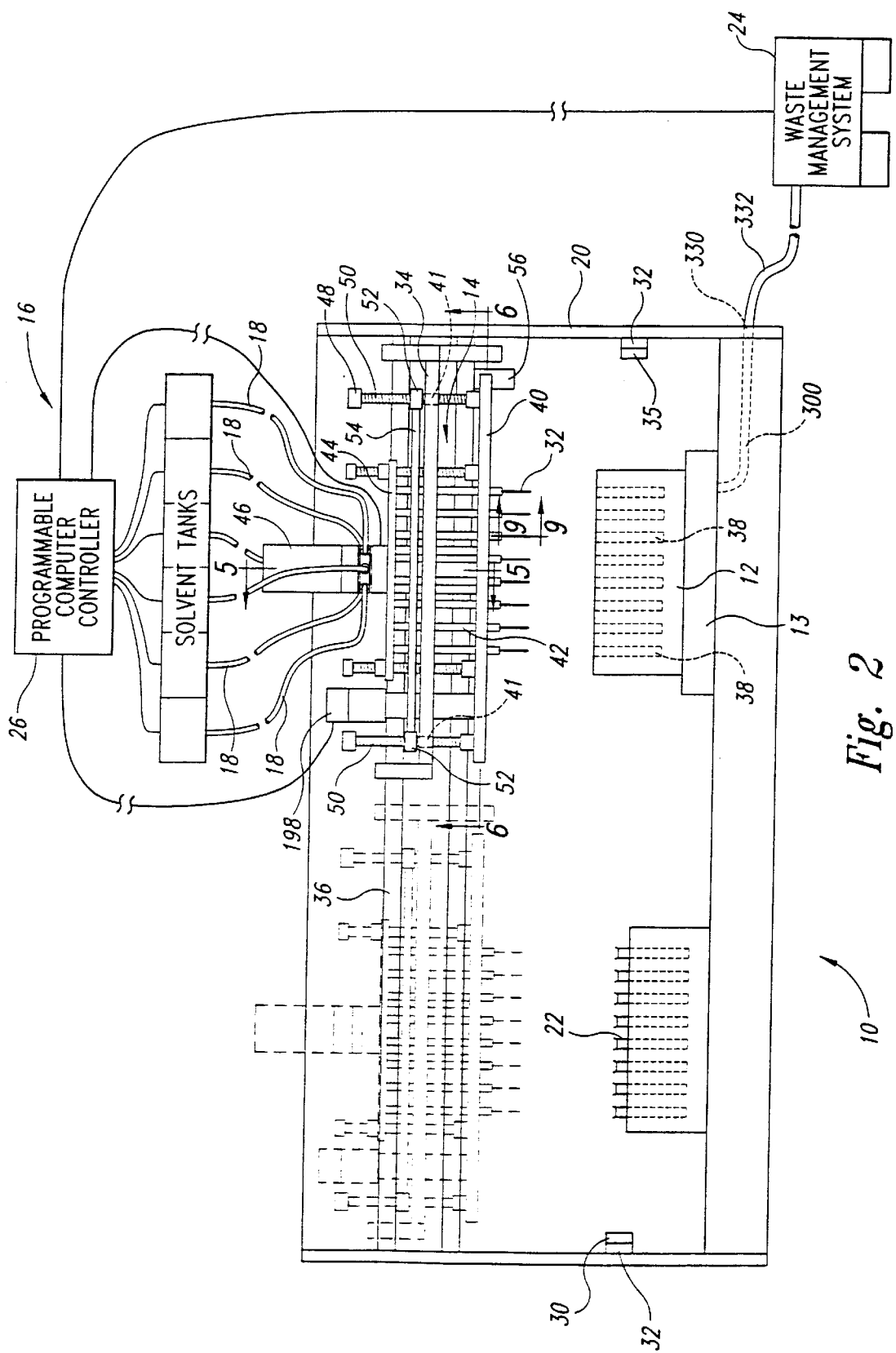
FIG. 2 is an enlarged front elevational view of the wash station of FIG. 1 showing the solvent dispensing assembly in solid lines in a raised position above the reaction chambers and showing the solvent dispensing assembly in phantom lines in the raised position over an array of rinse tubes.

As best seen in FIG. 2, the distributor support 34 and the dispensing assembly 14 are movable to a dispensing/aspirating position, shown in solid lines, wherein the dispensing assembly is positioned over the reaction blocks 12. The distributor support 34 and the dispensing assembly 14 are also movable to a rinse position, shown in phantom lines, wherein the dispensing assembly is positioned over the rinse tubes 22. The dispensing assembly 14 includes an array of ninety-six pipetting needles 32 for dispensing the selected solvent into the reaction chambers 38 in the reaction blocks 12, as discussed in greater detail below. When the dispensing assembly 14 is in the dispensing/aspirating position, each of the needles 32 is coaxially aligned with a separate reaction chamber 38, and when the dispensing assembly is in the rinse position, each needle 32 is coaxially aligned with a separate rinse tube 22.

Figure 3:
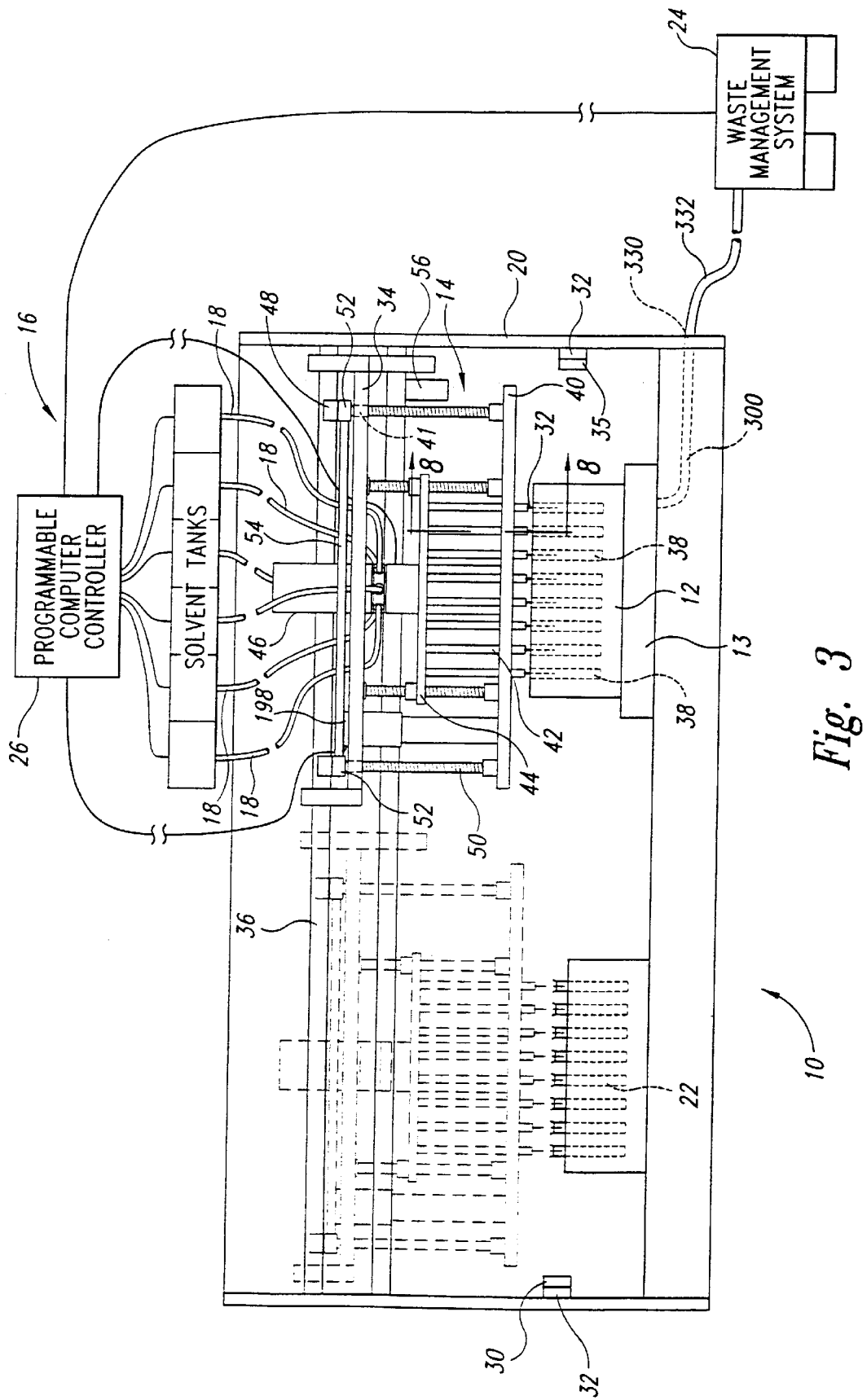
FIG. 3 is an enlarged front elevational view of the wash station of FIG. 1 showing the solvent dispensing assembly in solid lines in a lowered position above the reaction chambers, and showing the solvent dispensing assembly in phantom lines in the lowered position above the rinse tubes.

As best seen in FIGS. 2 and 3, the dispensing assembly 14 is also movable as a unit vertically relative to the distributor support 34 between a raised position (FIG. 2) and a lowered position (FIG. 3). When the dispensing assembly 14 is in the raised position, the needles 32 are above and out of engagement with the reaction blocks 12 or the rinse tubes 22. When the dispensing assembly 14 is in the lowered position and in the dispensing/aspirating position, shown in solid lines in FIG. 3, the needles 32 project into the reaction blocks 12 for dispensement of the solvent into the reaction chambers 38. When the dispensing assembly 14 is in the lowered position and in the rinse position, shown in phantom lines in FIG. 3, the needles 32 project into the rinse tubes 22 for rinsing.

Figure 4:
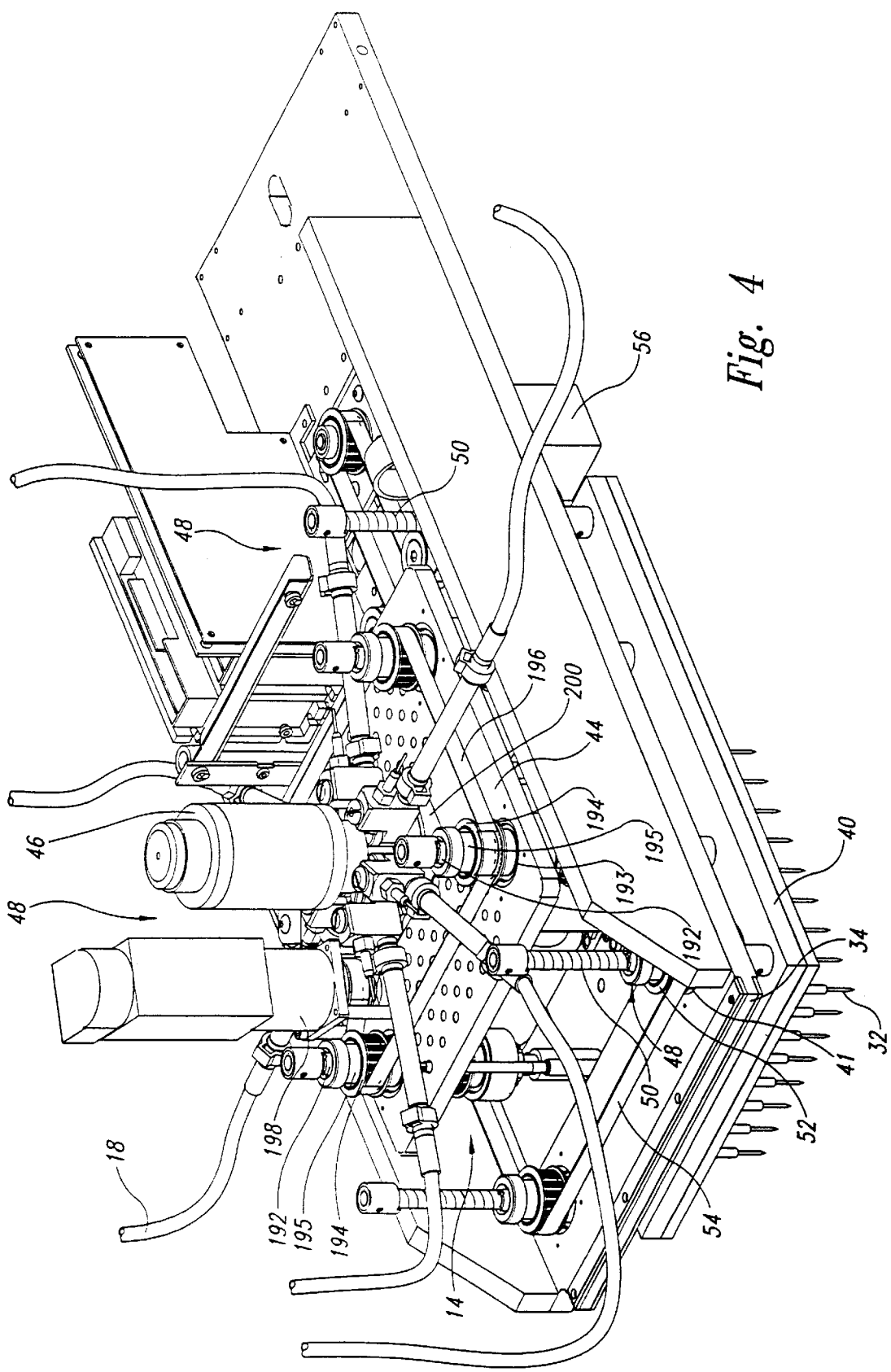
FIG. 4 is an enlarged top isometric view of a distributor support and a solvent dispensing assembly of the wash station of FIG. 1

As best seen in FIGS. 2–4, the dispensing assembly 14 is movably connected to the distributor support 34 by four ball-screw actuators 48. Each actuator 48 includes a threaded ball screw 50 that is fixed at its lower end to a lower distribution manifold 40 of the dispensing assembly 14. The ball screws 50 project upwardly through apertures 41 in the distributor support 34 and through a rotary drive mechanism 52 mounted to the distributor support. The rotary drive mechanism 52 threadably engages the ball screw 50 such that rotation of the drive mechanism causes axial movement of the ball screw relative to the distributor support 34.

The four drive mechanisms 52 on the distributor support 34 are interconnected by a drive belt 54, and the drive belt is connected to an electric drive motor 56 mounted on the distributor support 34. When the drive motor 56 is activated, it drives the drive belt 54, which simultaneously turns all four drive mechanisms 52. Accordingly, all four ball screws 50 are simultaneously moved axially, thereby uniformly raising or lowering the dispensing assembly 14 relative to the distributor support 34. In the exemplary embodiment, the drive motor 56 is operatively connected to the controller 26 such that the controller starts and stops the drive motor, thereby controlling the vertical position of the dispensing assembly 14.

The wash station 11 also includes safety features to provide safe automated operation of the assembly. An emergency stop button 28, shown in FIG. 1, is mounted on the frame and is operatively connected to the controller. Activation of the stop button 28 by a user immediately stops the wash cycle including all horizontal and vertical movement of the dispensing assembly 14. The wash station 11 will not function until it is reset via the controller 26.

The wash station 11 also has a light curtain assembly mounted to the frame 20 and positioned to create a light curtain around the frame's periphery. The light curtain assembly includes a light transmitter 30 mounted to the left side of the frame's back wall. The light transmitter 30 sends light beam out away from the back wall, and the light beam is directed around the frame's periphery by a pair of mirrors 32 mounted on the frame's front supports. The light beam is detected by a light detector 35 (shown in FIGS. 2 and 3) mounted on the right side of the frame's back wall opposite the light transmitter 30. The light curtain assembly is operatively connected to the controller such that the wash cycle is immediately terminated if the light curtain is interrupted. The wash station 11 will not function until it is reset by a user via the controller 26.

Solvent Dispensing Assembly

As best seen in FIGS. 2 and 3, the solvent dispensing assembly 14 includes an array of ninety-six syringes 42 connected to the distribution manifold 40 and to the array of needles 32. The syringes 42 receive solvent from the distribution manifold 40 and dispense the solvent through the needles 32. The syringes 42 extend between the distribution manifold 40 and an upper support plate 44 that is spaced apart from and parallel with the manifold. The distribution manifold 40 receives the solvent from a solvent selector valve 46 that is mounted to the distribution manifold. The selector valve 46 is connected to the six solvent lines 18 which carry the solvent from the pressurized solvent sources 16.

Figure 5:
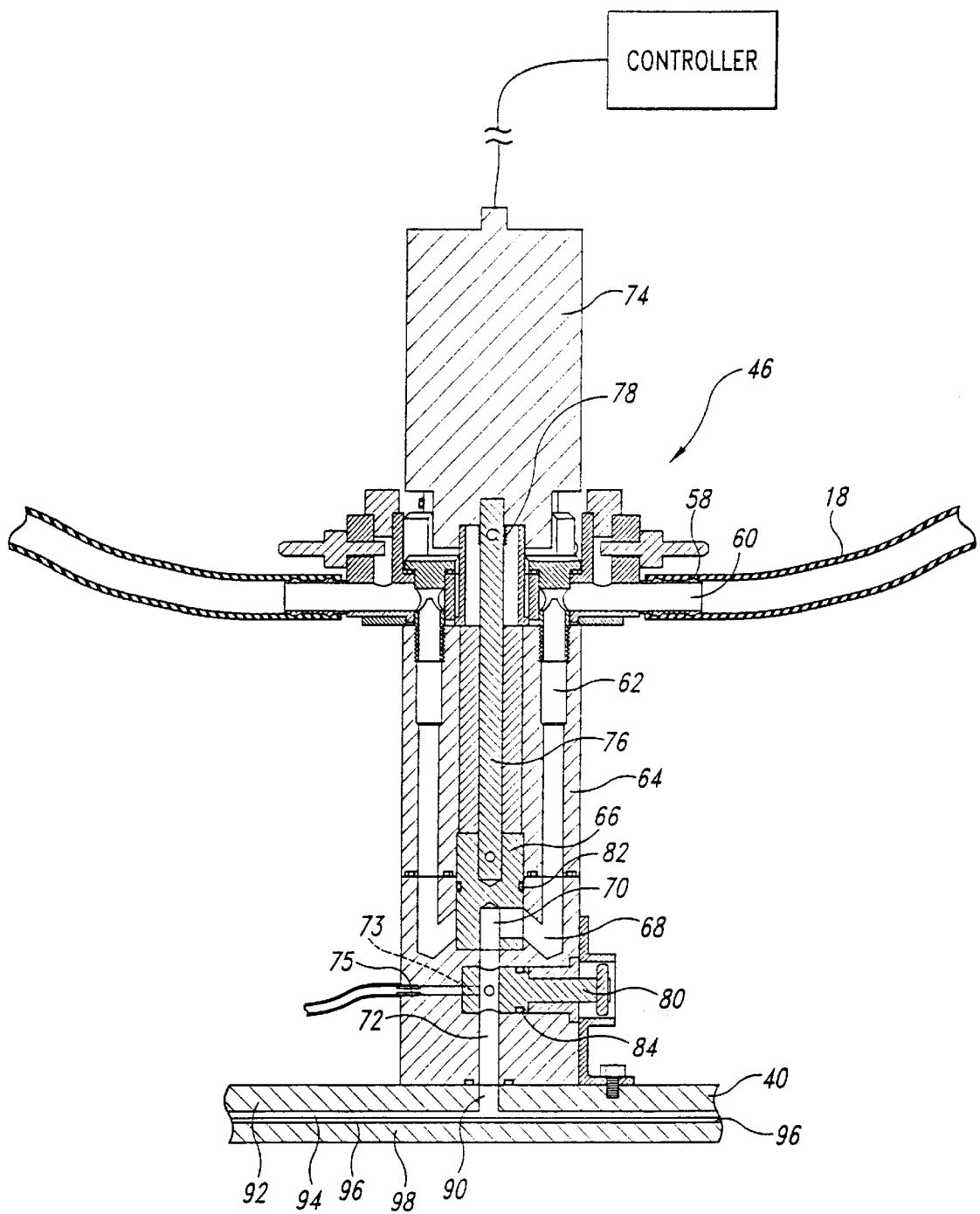
FIG. 5 is an enlarged cross-sectional view taken substantially along lines 5—5 of FIG. 2 showing a selector valve connected to solvent lines to a distribution manifold.

As best seen in FIG. 5, the selector valve 46 has a plurality of connectors 58 that each connect to a separate solvent line 18. In the exemplary embodiment, the selector valve 46 has six connectors 58 formed by hollowed banjo bolts, which connect to the six solvent lines 18. The selector valve's body 64 has six solvent passageways 62 formed therein, and each connector 58 has an interior passageway 60 that communicates with one of the solvent passageways 62 in the body 64.

The selector valve 46 has a rotary valve member 66 rotatably positioned. in the selector valve's body 64. The valve member 66 communicates with the open bottom ends 68 of each solvent passageway 62. The valve member 66 has an interior channel 70 that is positioned to communicate with the open bottom end 68 of only one solvent passageway 62 at a time, depending upon the selector valve's position The selector valve's interior channel 70 also communicates with an outlet passageway 72 in the selector valve's body 64. The outlet passageway 72 extends through the bottom portion of the selector valve's body 64 and communicates with the distribution manifold 40. Accordingly, the selector valve 46 allows only one of the six solvents to pass therethrough at a time, so that the one selected solvent flows into the distribution manifold 40. The valve member 66 blocks the other five solvent passageways 62 and prevents those solvents from flowing out of the other solvent passageways.

The selector valve 46 has an actuator 74 that is connected to the top of the selector valve's body 64 and connected to an upper end 78 of a shaft 76, which is secured to the valve member 66. The valve's actuator 74 rotates the shaft 76 and the valve member 66 within the valve's body 64 to align the interior channel 70 with a selected solvent passageway 62. The actuator 74 is operatively connected to the controller 26, such that the controller can activate the actuator to position the valve member 66 in a desired position to allow the selected solvent to pass through the selector valve 46. The actuator 74 also includes a position sensor that is coupled to the controller, so the controller can determine the relative position of the valve member 66, thereby determining which solvent is passing through the selector valve.

The selector valve 46 of the exemplary embodiment has a gate valve 80 mounted in the bottom portion of the selector valve's body 64. The gate valve 80 is partially positioned within the outlet passageway 72 and is movable between open and closed positions. The gate valve 80 is moved between the open and closed positions by an actuator similar to the actuator 74 discussed above. When the gate valve 80 is in the open position, solvent can freely pass through the outlet passageway 72 into the distribution manifold 40. When the gate valve 80 is in the closed position, the solvent is blocked from passing through the outlet passageway 72 into the distribution manifold 40.

The gate valve 80 includes a pressure relief passageway 73 therethrough that communicates with the outlet passageway 72 when the gate valve is in the closed position. The pressure relief passageway 73 is connected to an outlet channel 75 extending through the selector valve's body 64, and the outlet channel 75 is open to atmospheric pressure. The pressure relief passageway 73 allows the release of back-pressure in the interior channel 72, thereby minimizing back pressure within the distribution manifold when the gate valve 80 is in the closed position. When the gate valve 80 is open, the pressure relief passageway 73 is aligned so it does not communicate with the outlet passageway 72, as shown in FIG. 5.

In the exemplary embodiment, the selector valve's body 64 is manufactured of a Teflon material and the rotary valve member 66 is press fit into an aperture formed in the body. An O-ring 82 is connected to the valve member 66 and sealably engages the body to prevent solvent from migrating upwardly between the valve member and the body. An O-ring 84 is also connected to the gate valve 80 and sealably engages the selector valve's body 64 to prevent migration of solvent past the O-ring. Accordingly, all of the solvent passing through the selector valve is directed to the distribution manifold.

Distribution Manifold

As best seen in FIG. 5, the distniution manifold 40 has a manifold inlet 90 that communicates with the selector valve's outlet passageway 72 and receives the solvent which has passed through the selector valve 46. In the exemplary embodiment, the distribution manifold 40 is formed by an upper manifold plate 92, a gasket 96, and a lower manifold plate 98 that sandwiches the gasket between the upper and lower manifold plates. The upper manifold plate 92 has ninety-six distribution channels 94 formed therein for distributing the solvent throughout the manifold. The gasket 96 sealably engages the upper manifold plate 92 without impinging on the distribution channels 94 so as to allow the solvent to freely flow through the distribution channels.

Figure 6:
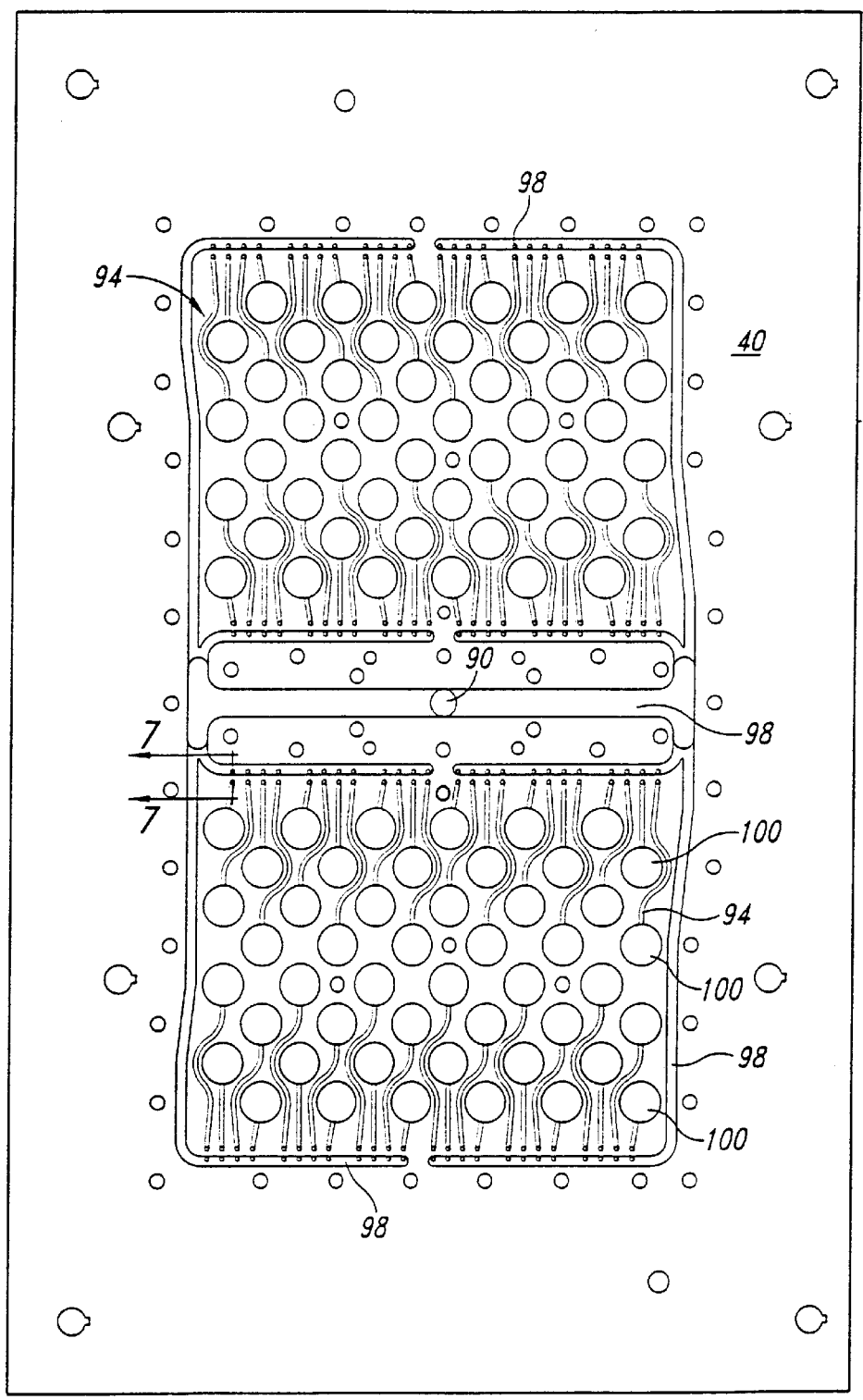
FIG. 6 is an enlarged cross-sectional view taken substantially along lines 6—6 of FIG. 2 showing a distribution manifold having a plurality of distribution channels that distribute the solvent to syringe apertures that receive the syringes (not shown) therein.

As best seen in FIG. 6, the manifold inlet 90 communicates with outlet channels 98 that, in turn, communicate with the ninety-six distribution channels 94. Each distribution channel 94 communicates with a syringe aperture 100 that threadably receives one of the syringes 42 (not shown). Accordingly, the distribution manifold 40 equally distributes the solvent through the distribution channels 94 to every syringe aperture 100 to allow the solvent to be drawn into every syringe.

In the exemplary embodiment, the solvent is provided to the selector valve 46 and the distribution manifold 40 under positive pressure, so the solvent is equally distributed throughout the distribution channels 94 to the syringes 42. The pressure under which the solvent is provided is selected to ensure there is equal and accurate distribution to each and every syringe 42. The pressure of the solvent is monitored by a pressure sensor on the selector valve 46 and coupled to a pressurization system connected to the solvent sources 16. If the pressure of the solvent at the selector valve 46 is insufficient, the pressure in the particular solvent source 16 is adjusted to provide the solvent at the desired pressures. This extent of pressure adjustment is determined in part by the density and viscosity of the particular solvent and the pressure drop between the solvent source and the selector valve 46.

Figure 7:
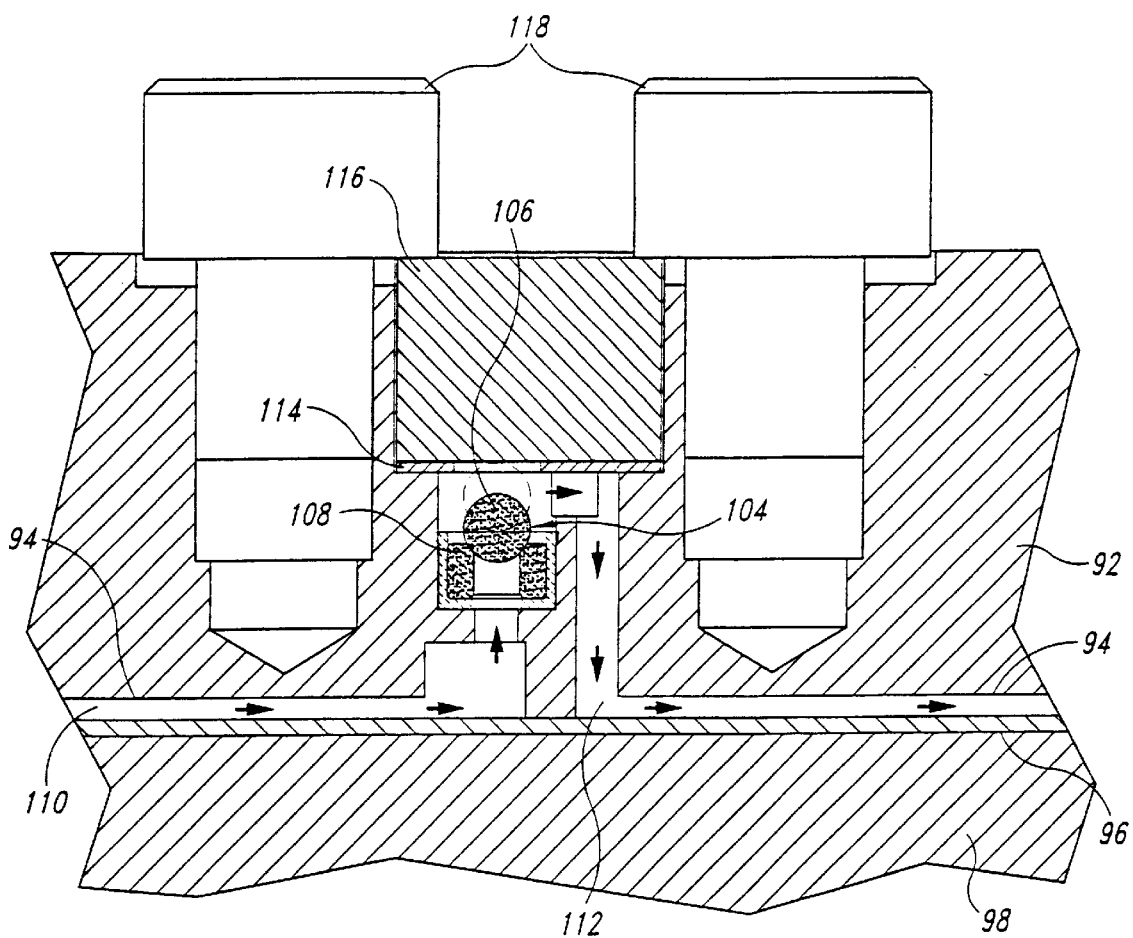
FIG. 7 is an enlarged cross-sectional view taken substantially along lines 7—7 of FIG. 6 showing a manifold valve in a closed position in solid lines and in an opened position in phantom lines.

As best seen in FIG. 7, each distribution channel 94 includes a ball-type check valve 104 that is movable between an open position, shown in phantom lines, and a closed position, shown in solid lines. The check valve 104 prevents backflow of the solvent through the distribution channels 94. The check valve 104 includes a ball 106 movably positioned on a valve seat 108. The check valve 104 communicates with an upstream portion 110 of the distribution channel 94 and receives the solvent flow through the upstream portion. The solvent flows out of the check valve 104 through a downstream portion 112 of the distribution channel 94.

When the check valve 104 is in the open position, shown in phantom lines, the ball 106 is lifted or displaced from the valve seat 108 and solvent flows from the upstream portion 110, through and out the downstream portion 1 2. Accordingly, the solvent can flow freely to the respective syringe aperture 100 (FIG. 6). When the check valve 104 is in the closed position, the ball 106 is sealably on the valve seat 108, thereby preventing the solvent from backflowing into the upstream portion 110 of the distribution channel 94 toward the manifold inlet.

In the exemplary embodiment, the check valve 104 includes a gasket 114 and a valve cover 116 that are positioned above the ball 106 to limit the vertical displacement of the ball and to retain the ball adjacent to the valve seat 108. The valve cover 116 and gasket 114 are secured in place by a plurality of fasteners 118. If maintenance is required for the check valve 104, or if the ball 106 becomes blocked or jammed, it can be repaired by removing the fasteners 118, the valve cover 116, and the gasket 114, thereby providing access to the ball and the valve seat 108.

Syringe and Needle

Figure 8:
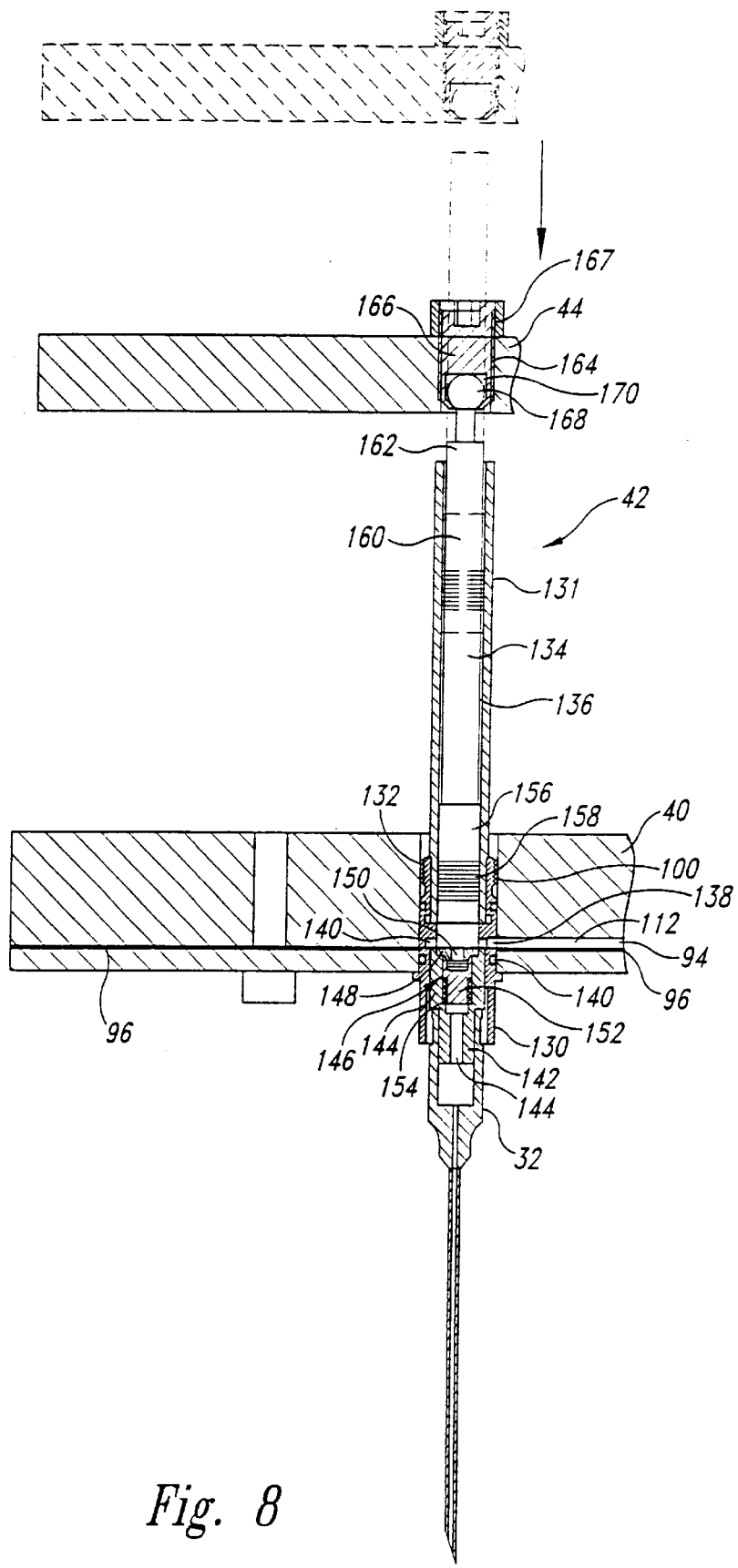
FIG. 8 is an enlarged cross-sectional view taken substantially along lines 8—8 of FIG. 3 showing a syringe and a pipetting needle.

As best seen in FIG. 8, each syringe 42 includes a bottom connector 130, a barrel 131 fixedly connected to the connector, and a plunger 134 slidably positioned within the barrel. The connector 130 and barrel 131 define an interior area 136 of the syringe that is adapted to receive a selected amount of the solvent therein. The distribution manifold 40 directs the solvent into each syringe 42 through a pair of inlet apertures 140 in the connector 130, which is removably positioned in a respective syringe aperture 100. The connector 130 has a plurality of threads 132 that engage the distribution manifold 40 and retain the syringe 42 in the syringe aperture 100. The connector 130 has an annular groove 138 that communicates with the downstream portion 112 of the manifold's distribution channel 94 for that syringe. The inlet apertures 140 are positioned in the annular groove 138 and connected to the syringe's interior area 136. Accordingly, the solvent flows into the annular groove 138 and enters the syringe's interior area 136 through the inlet apertures 140.

The connector 130 also includes a connection portion 142, such as a Luer connector, that is adapted to removably connect to the pipetting needle 32. The connection portion 142 has an outlet passageway 144 therethrough that is coaxially aligned with and in communication with the syringe's interior area 136. The outlet passageway 144 allows the solvent in the syringe's interior area 136 to be pushed out of the barrel 131 by the plunger 134, thereby forcing the solvent into and through the pipetting needle 32.

The connector 130 in the exemplary embodiment includes a check valve 146 positioned in the outlet passageway 144 to prevent backflow from the pipetting needle 32 into the syringe 42. The check valve 146 is movable between open and closed positions. In the open position, so solvent can flow out of the syringe's interior area 136 through the outlet passageway 144. In the closed position, the check valve 146 prevents fluid from backflowing through the valve seat 148.

In the exemplary embodiment, the check valve 146 is biased toward the closed position by a spring 154 positioned in the outlet passageway 144. The spring's resistance is selected to allow the check valve 146 to open when the solvent is dispensed from the syringe 42 through the pipetting needle 32. In one embodiment, the check valve 146 is a poppet valve formed with an elastomeric compound, such as a Perfluoroelastomer, known commercially as Stilrez Chemrez, or Kalrez that sealably engages a valve seat 148. The elastomeric compounds must be sufficiently durable for use with the solvents typically utilized during generation of combinatorial chemical libraries.

Referring again to FIG. 8, the syringe's plunger 134 is axially movable within the barrel 131 to draw solvent into the syringe's interior area 136 and to dispense the solvent from the syringe. The plunger 134 includes a plunger tip 156 having a plurality of flexible ribs 158 that sealably engage the walls of the barrel 131. In exemplary embodiments, the syringe's barrel 131 is a glass or stainless steel barrel that provides for a very smooth surface for an efficient and effective seal between the barrel and the plunger tip's ribs 158.

The plunger tip 156 is connected to a plunger rod 160 that projects out of the barrel's open upper end. The plunger rod 160 is connected at its upper end 162 to a respective adjusting screw 166 mounted in an aperture 164 in the upper support plate 44. The plunger rod's upper end 162 includes a ball swivel 168 that is rotatably captured in a receiving pocket 170 in the adjusting screw 166. Accordingly, the plunger rod's axial alignment within the barrel 131 is adjustable so as to prevent the plunger rod 134 from binding within the barrel during the discharge or aspirating strokes. A locking nut 167 is secured to the adjusting screw 166 to lock the adjusting screw and plunger rod 160 in place after the plunger rod is adjusted to its proper axial position.

In the exemplary embodiment, the adjusting screw 166 is removably connected to the upper support plate 44, so the adjusting screw and the plunger 134 can be quickly and easily removed as a unit and replaced. Similarly, the syringe's connector 130 and barrel 131 can be removed and replaced by unscrewing the connector from the distribution manifold 40 and removing it from the syringe aperture 100. A replacement or repaired syringe can then be easily and quickly reinstalled into the syringe aperture 100, thereby minimizing down time of the wash station assembly 10 for maintenance or repairs.

As best seen in FIG. 8, the plunger 134 is movable axially within, the barrel 131 between a lowered, dispensed position, shown in solid lines, and a raised, aspirated position, shown in phantom lines. As the plunger 134 is moved from the lowered, dispensed position axially toward the raised, aspirated position, solvent is drawn into the syringe's interior area 136 through the inlet aperture 140 in the syringe's connector 130. When the plunger is fully moved to the raised, aspirated position, the syringe 42 is loaded with a predetermined amount of the solvent.

When the syringe 42 is loaded and the plunger 134 is moved through a discharge stroke to the lowered, dispensed position, the plunger tip 156 forces the solvent out of the syringe. The volume of the solvent dispensed is closely controlled by controlling the stroke length during the aspirating as the plunger 134 is moved from the raised, aspirated position.

Dispensing of the solvent is also closely controlled, depending upon the solvent and the washing process being performed. In one embodiment, the plunger's dispensing stroke is a continuous stroke from the raised aspirated position to the lowered dispensed position to provide a continuous flow into the reaction chamber. In an alternate embodiment, the dispensing stroke includes a pulsating stroke, wherein the plunger stops periodically at intermediate positions between the raised, aspirated position and the lowered, dispensed position, thereby providing a pulsating dispensement of the solvent into the reaction chamber.

Figure 9:
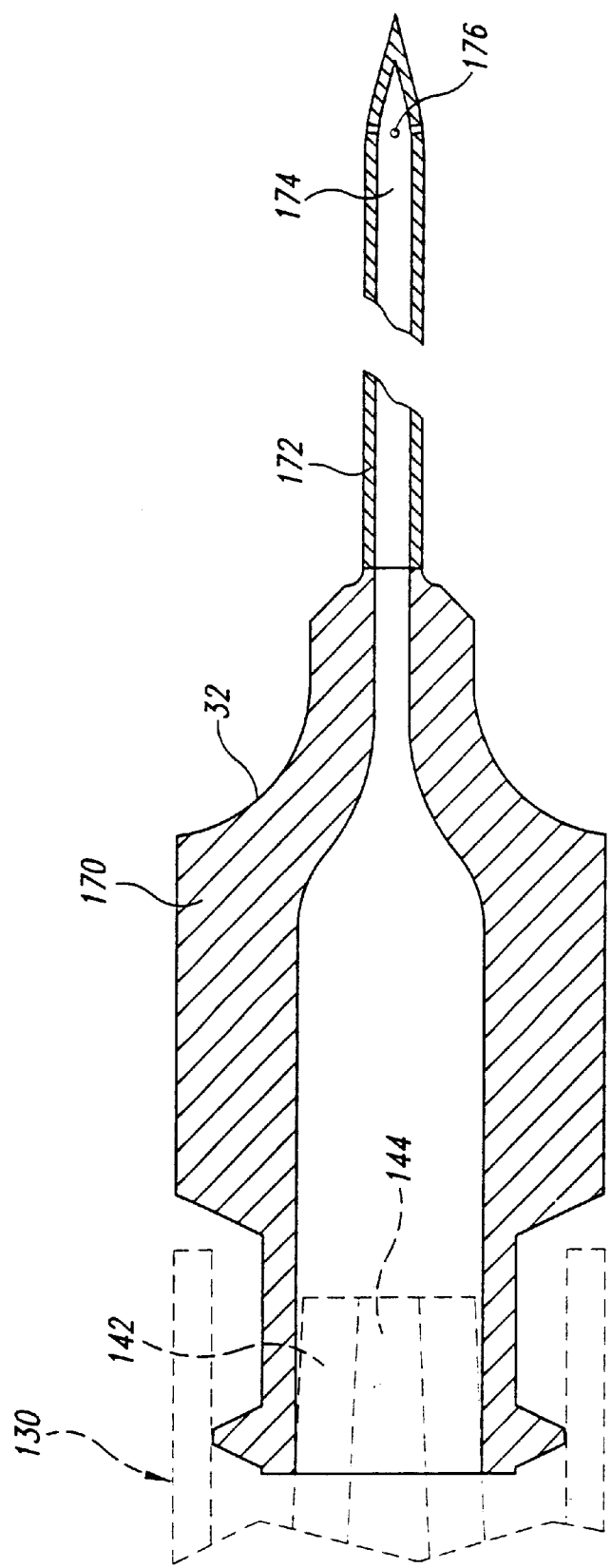
FIG. 9 is an enlarged cross-sectional view taken substantially along lines 9—9 of FIG. 3 showing the pipetting needle.

As best seen in FIG. 9, the pipetting needle 32 has a conventional Luer lock hub 170 that removably connects to the connection portion 142 of the syringe's connector 130. The pipetting needle 32 includes a hollow shaft 172 with an interior channel 174 that receives the solvent from the syringe's connector 130. The distal end of the needle's shaft 172 includes a plurality of substantially radially directed apertures 176 that communicate with the hollow needle's interior channel 174. The radially directed apertures 176 are sized to allow the solvent passing through the needle 32 to be dispensed radially outwardly relative to the needle.

In the embodiment illustrated in FIG. 9, the pipetting needle 32 includes a sharp pencil-point end that facilitated piercing the septum of the reaction blocks 12 discussed above. The pencil-point end also facilitates the radial dispensing of the solvent through the apertures 176.

When the pipetting needle 32 is positioned in the respective reaction chamber 38 in the reaction block 12 (FIG. 3) and the solvent is dispensed, the radially directed apertures 176 direct the solvent onto the sides of the reaction chambers for a full and complete washing of the reaction chamber including the solid phase sample therein. In an alternate embodiment of the invention, the needles 32 have a plurality of radially directed slots in the distal end of the needle's shaft to provide a different radial distribution pattern of the solvent. In another alternate embodiment of the invention, the pipetting needles 32 have an axially aligned outlet aperture at the point of the needle's shaft, so the solvent is dispensed axially from the needle.

Aspirating and Dipensing Strokes of the Syringe

Figure 10:
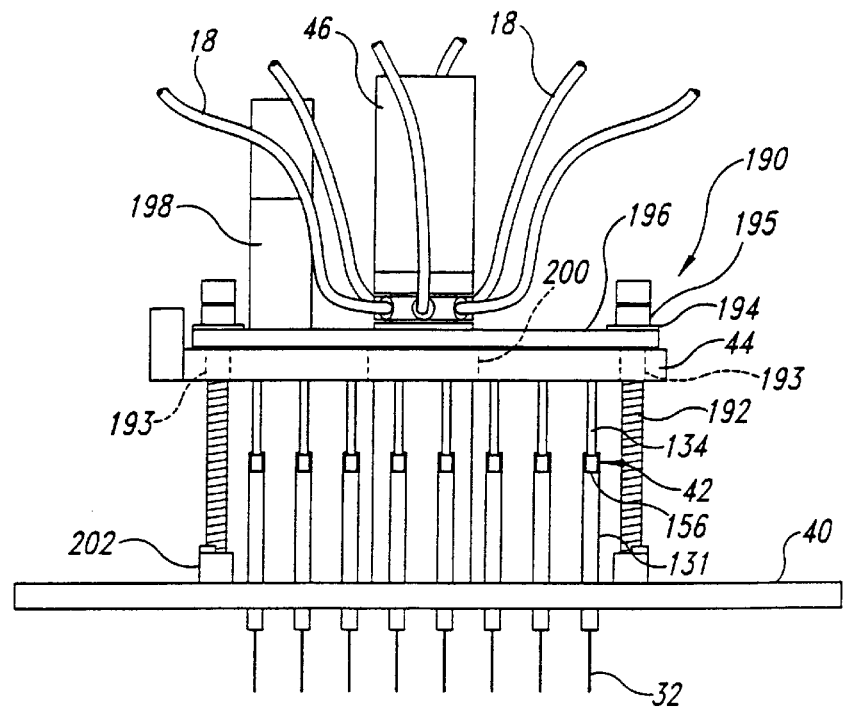
FIG. 10 is an enlarged partial front elevational view of the solvent dispensing assembly of FIG. 1 shown removed from the wash station and shown in a dispensing position ready to dispense solvent from the syringes.
Figure 11:
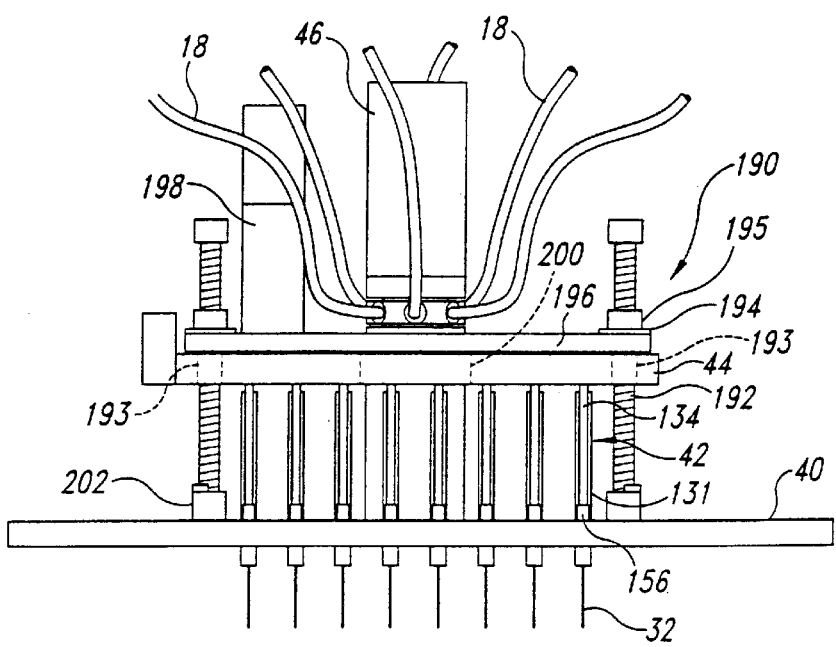
FIG. 11 is an enlarged partial front elevational view of the solvent distribution of FIG. 1 with the solvent dispensing assembly shown removed from the wash station and shown in an aspirating position ready to aspirate and draw solvent into the syringes.

In the exemplary embodiment, as shown in FIGS. 10 and 11, the syringe's plunger 134 is moved axially within the barrel 131 along the aspirating and dispensing strokes by moving the upper support plate 44 relative to the distribution manifold 40. The upper support plate 44 is movably connected to the distribution manifold 40 by a plurality of actuators 190. Each actuator 190 includes a ball screw 192 that is fixedly attached at its bottom end to the distribution manifold 40. Four ball screws 192 extend through apertures 193 in the upper support plate 44 and connect to drive mechanisms 194 rotatably mounted on the upper support plate 44. The drive mechanisms 194 include rotatable ball nuts 195 that threadably engage the ball screws 192, such that rotation of the ball nuts causes axial movement along the axis of the ball screws, thereby moving the upper support plate 44 to move toward or away from the distribution manifold 40.

The drive mechanisms 194 are interconnected by a drive belt 196 that is operatively connected to a drive motor 198 mounted to the upper support plate 44. The drive motor 198 is operatively connected to the controller 26 (not shown) such that the drive motor is selectively started and stopped by the controller. In the exemplary embodiment, the drive motor 198 includes an encoder that communicates with the controller 26 for highly accurate control of the drive motor, thereby providing highly accurate control of the plunger's position within the syringe 42 for accurate aspirating and dispensing of the solvent.

The upper support plate 44 is movable relative to the distribution manifold 40 to a raised position (as shown in FIG. 10) so as to position the plunger 134 in the raised, aspirated position. The upper support plate 44 is also movable to a dispensed position, as shown in FIG. 11. In this dispensed position, the upper support plate 44 is positioned such that the plunger' tip 156 is positioned substantially against a valve seat 148 of the check valve 146. As the actuators 190 drive the upper support plate 44 from the dispensed position toward the raised position, the plunger 134 moves through the aspirating stroke to draw a selected amount of the solvent into the barrel for subsequent dispensing into the reaction chambers of the reaction blocks (not shown). As the actuators 190 drive the upper support plate 44 from the raised position to the dispensed position, the plunger 134 moves through the dispensing stroke so all of the solvent is fully dispensed from the syringe 42.

In the exemplary embodiment illustrated in FIGS. 10 and 11, the movement of the upper support plate 44 relative to the distnbution manifold 40 is stopped when the upper support plate reaches the lowered position by a rotary stop mounted on the ball screw 192. The rotary stop is positioned to block further rotational movement of the drive mechanism 194 when the upper support plate reaches the lowered position. Such radial blocking provides an effective stop mechanism against further movement of the upper support plate, without generating axial loads on the upper support plate 44 or the distribution manifold 40, thereby preventing damage to the syringes 42.

In the exemplary embodiment, the upper support plate 44 has an enlarged aperture 200 therein, and the selector valve 46 is positioned in the enlarged aperture. Accordingly, as the upper support plate 44 moves between the raised position and the lowered position, the upper support plate moves relative to the selector valve without any interference by the selector valve 46 or the solvent lines 18.

Pressurized Solvent Tank and Level Sensing System

The solvent dispensing assembly 14 receives the solvent from the six solvent tanks 16 through the solvent lines 18, as shown in FIGS. 1 and 2. The solvent tanks 16, in the exemplary embodiment, are pressurized with Nitrogen gas, although another inert gas or air could also be used. The solvent tanks 16 are maintained at a selected pressure so as to provide solvent to the selector valve 46 at the desired pressure to ensure equal and accurate distribution to all of the syringes 42 taking into account pressure drops in the system and the solvent's density and viscosity, as discussed above.

The pressure in each solvent tank 16 is controlled based upon the pressure in the solvent line at the selector valve 46. The selector valve 46 includes pressure sensors that determine the pressure at which the solvent is provided to the selector valve. The pressure sensors are connected to the controller 26, which monitors the pressure of the solvents at the selector valve. If the pressure for a particular solvent needs to be increased or decreased, the controller 26 increases or decreases the pressure in the respective solvent tank 16 until the desired pressure is achieved.

Figure 13:
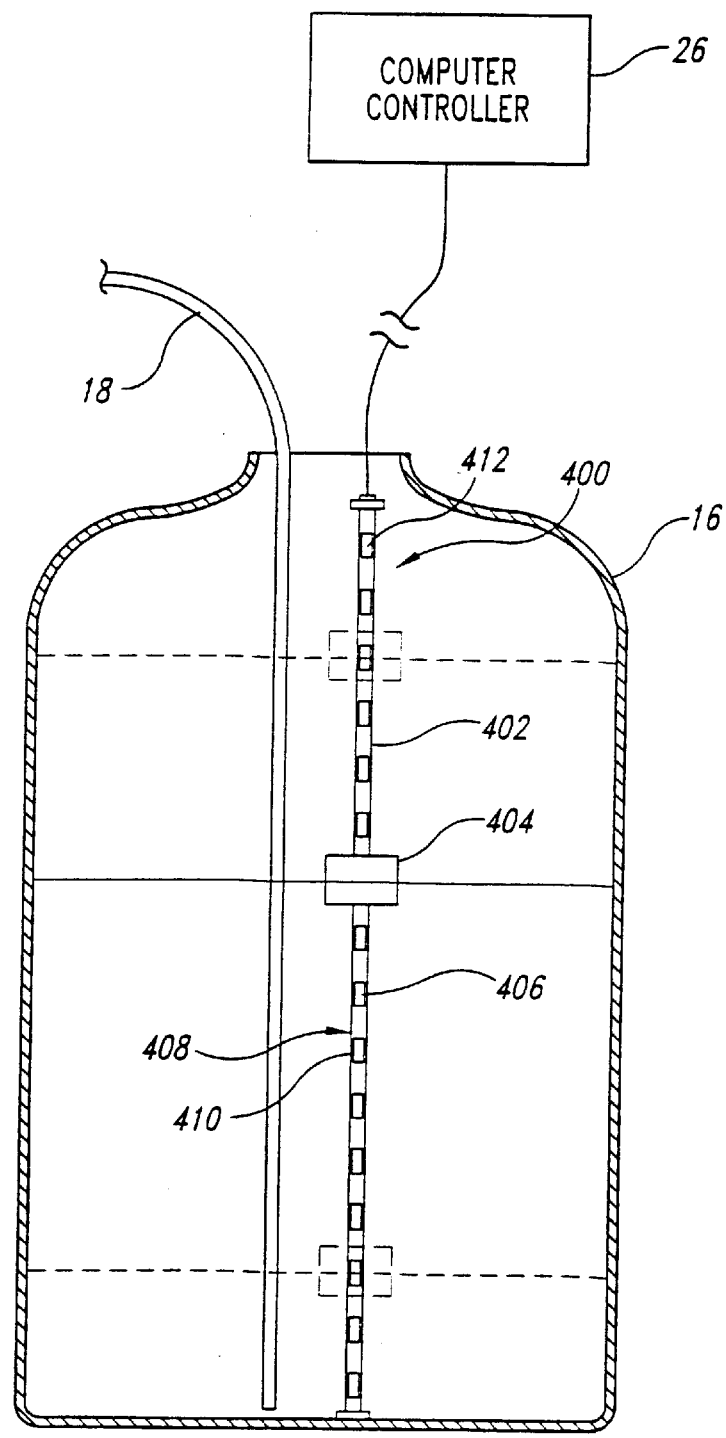
FIG. 13 is an enlarged cross-sectional view of a solvent tank of FIG. 2, showing a solvent level sensing system.

As best seen in FIG. 13, each solvent tank 16 also includes a level sensing system 400 that identifies how much solvent is in the respective tank. Each level sensing system 400 is connected to the controller 26. The controller 26 monitors the solvent levels and provides an indication to an operator when the solvent level is too low. The user can then change solvent tanks to provide a full tank.

The level sensing system 400 is positioned within a solvent tank 16 and has a tube 402 that extends between the top and bottom of the tank. Accordingly, the tube 402 is at least partially positioned within the solvent in the tank 16. A magnetic float 404 is slidably positioned on the tube 402 and is adapted to float on the solvent's surface. The magnetic float 404 moves with the solvent level, so as the solvent level drops, the magnetic float moves downwardly along the tube 402.

A plurality of vertically spaced magnetic reed switches 406 are contained in the tube and are spaced close enough together so that at least one reed switch is energized by the magnetic float 404 at all positions along the tube. In the exemplary embodiment, the reed switches 406 are mounted along the tube on ½-inch centers.

Figure 14:
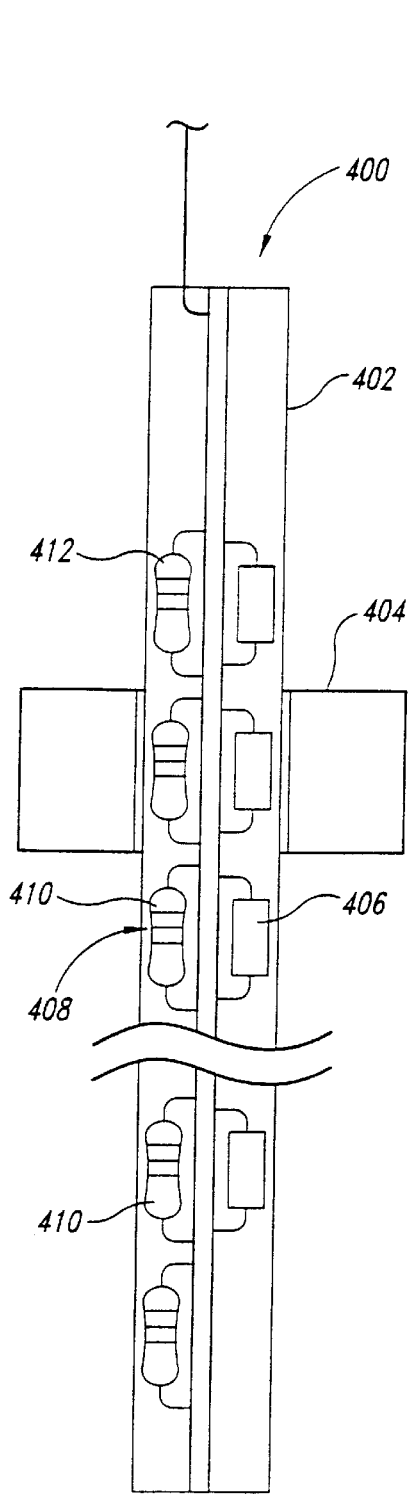
FIG. 14 is an enlarged cross-sectional view of a tube, magnetic float, resistors, and reed switches of the level sensing system of FIG. 13.
Figure 15:
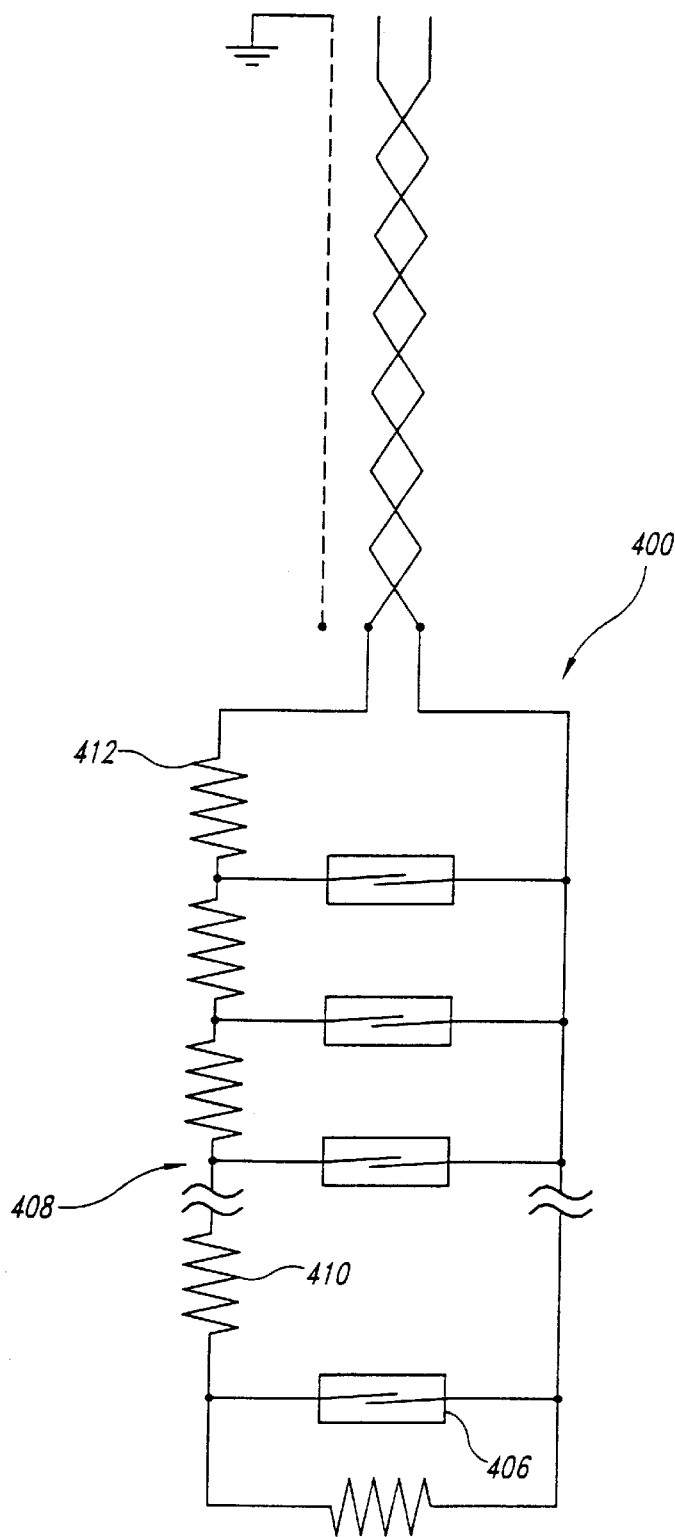
FIG. 15 is a schematic electrical diagram of the level sensing system of FIG. 13.

As best seen in FIGS. 14 and 15, the reed switches 406 are connected to a resistance ladder 408 that includes a plurality of resistors 410 of equal resistance connected in series and connected to the reed switches. The total resistance value of the level sensing system 400 is inversely proportional to the vertical position of the magnetic float 404 along the tube 402. As the magnetic float 404 (FIG. 14) moves down along the tube as the solvent level drops, the reed switches 406 are sequentially energized, thereby incrementally changing the resistance in the resistance ladder 408.

The level sensing system 400 is adapted to sense fluid levels in ½-liter increments in 1, 3, 5, and 10 gallon tanks 16, which can be used with the wash station assembly. The resistor ladder 408 for each size tank includes a coding resistor 412 that is used to establish a reference resistance value for that resistor ladder. The coding resistors 412 for the different size tanks have different resistance values so the computer controller 26 can identify which size tanks are connected to the wash station 11. For example, a coding resistor 412 for a first tank size (e.g., 10 gallon) is coded with a value of zero ohms (i.e., a straight wire). The coding resistor 412 for a second size tank (e.g., 5 gallon tank) is coded with a value that is greater than the maximum resistance for the first tank size, which is the combination of the resistors 410 and the coding resistor. Accordingly, there is no overlap between the resistance ranges of the different tank sizes, thereby allowing the computer controller to differentiate between tank sizes.

In the exemplary embodiment, the level sensing system 400 is connected to a constant current source with a low voltage (i.e., 9V) maximum input. The current source is fed through a current limiting resistor to the resistance ladder 408. Only two active wires and a shield for ground purposes are connected to the level sensing system 400 to achieve the low voltage, low current level sensing function. The computer controller 26 monitors the voltage and resistance of the resistance ladder, and is programmed to identify the float's vertical position based upon that voltage and resistance from the resistance ladder. The voltage is proportional to the value of the coding resistor 412 plus the resistance of the resistor ladder 408 given the highest reed switch 406 that is energized by the magnetic float 404 at the time.

The controller 26 determines that the amount of solvent in the selected tank 16 before initiation of a wash cycle. If the tank 16 has enough solvent in it, the controller 26 will start the wash cycle. It however, the controller 26 determines that the tank 16 does not have enough solvent in it, the controller will not initiate the wash cycle. The controller 26 provides an indication to the operator of the low solvent tank.

Waste Disposal and Waste Management System

After the selected solvent is dispensed into the reaction blocks 12, the solvent is allowed to sit in the reaction chambers 38 or is shaken by the vortexing shaker connected to the docking station 13. The solvent is then drained from the reaction chambers 38 by applying positive pressure or a partial vacuum to the reaction blocks 12. In the exemplary embodiment, positive pressure is generated by pressurized Nitrogen that is carried to the reaction blocks 12 by a plurality of Nitrogen lines 301, shown in hidden lines in FIG. 1. The flow of pressurized Nitrogen is controlled by conventional nitrogen control valves coupled to the Nitrogen lines 301. The wash station 11 also has a drain line 300 connected to the docking station 13 to receive the solvent drained from the reaction blocks 12.

Figure 12A:
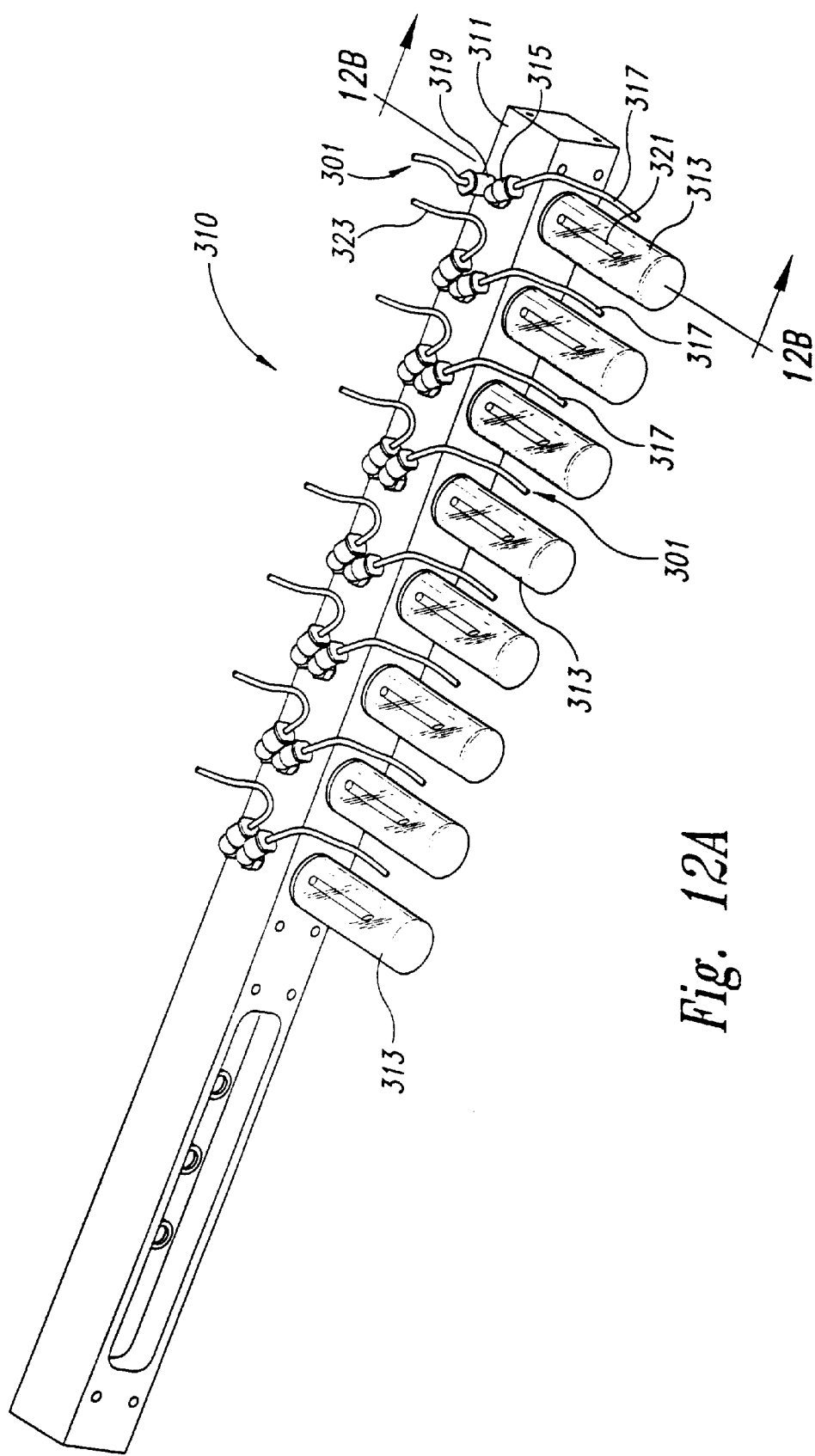
FIG. 12A is an enlarged bottom isometric view of a liquid back flow protection assembly of the wash station of FIG. 1 shown removed from the wash station.

The Nitrogen lines 301 are connected to a back flow protection assembly 310 connected to the frame 20 below the platform 15. As best seen in FIG. 12A, the backflow protection assembly 310 includes a mounting bar 311 that is fastened to the frame 20 (not shown) and eight liquid trap bottles 313 that are coupled to the Nitrogen lines 301. The backflow protection assembly 310 prevents any liquids from flowing back into the nitrogen lines and causing damage to the nitrogen control valves.

Figure 12B:
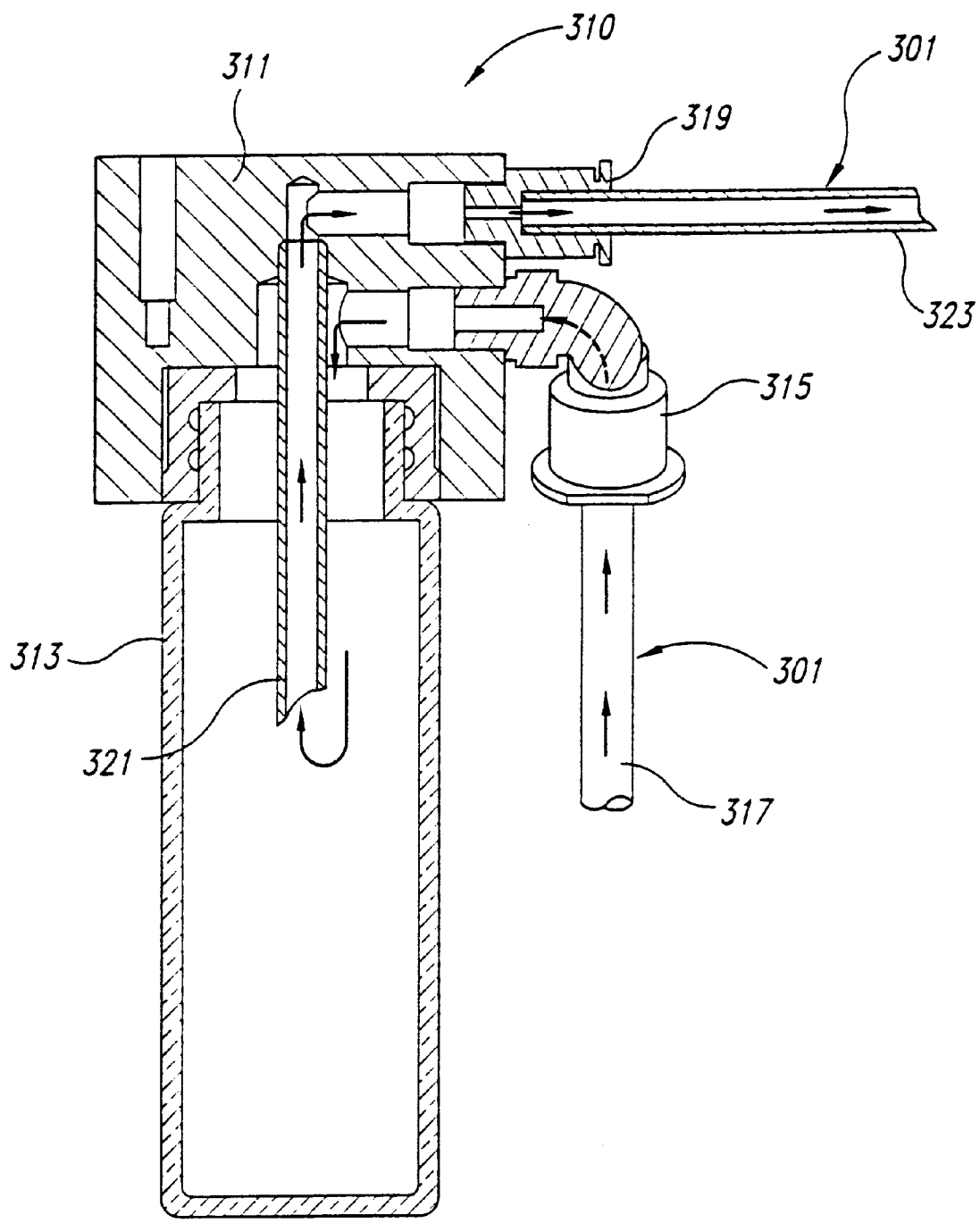
FIG. 12B is an enlarged cross-sectional view taken substantially along lines 12B—12B of FIG. 12A showing the back flow protection assembly.

As best seen in FIGS. 12A and 12B, the backflow protection assembly 310 includes an inlet port 315 connected to the mounting bar 311 and connected to an upstream portion 317 of a Nitrogen line 301. The inlet port 315 communicates with the interior area of the respective liquid trap bottle 313. An outlet port 319 is connected to the mounting bar 311 and to a downstream portion 323 of the Nitrogen line 301. The outlet port 319 is also connected to a trap tube 321 that extends into the liquid trap bottle 313. The trap tube 321 extends only partially into the bottle's interior area and terminates above the bottom of the bottle. Any back flow of liquid through the Nitrogen line's downstream portion 323 will flow through the outlet port 319 and the tube 321 and will collect in the bottom of the liquid trap bottle 313. Therefore, the liquid will not back flow through the Nitrogen line's upstream portion 317 and damage the Nitrogen control valves.

The drain line 300 shown in FIG. 1 is connected to an outlet port 330 of the wash station 11, and the outlet port is connected to a waste line 332 from the waste management system 24. Accordingly, the waste solvent exits the wash station 11 through the outlet port 330 and enters the waste management system 24 through the waste line 332.

Figure 16:
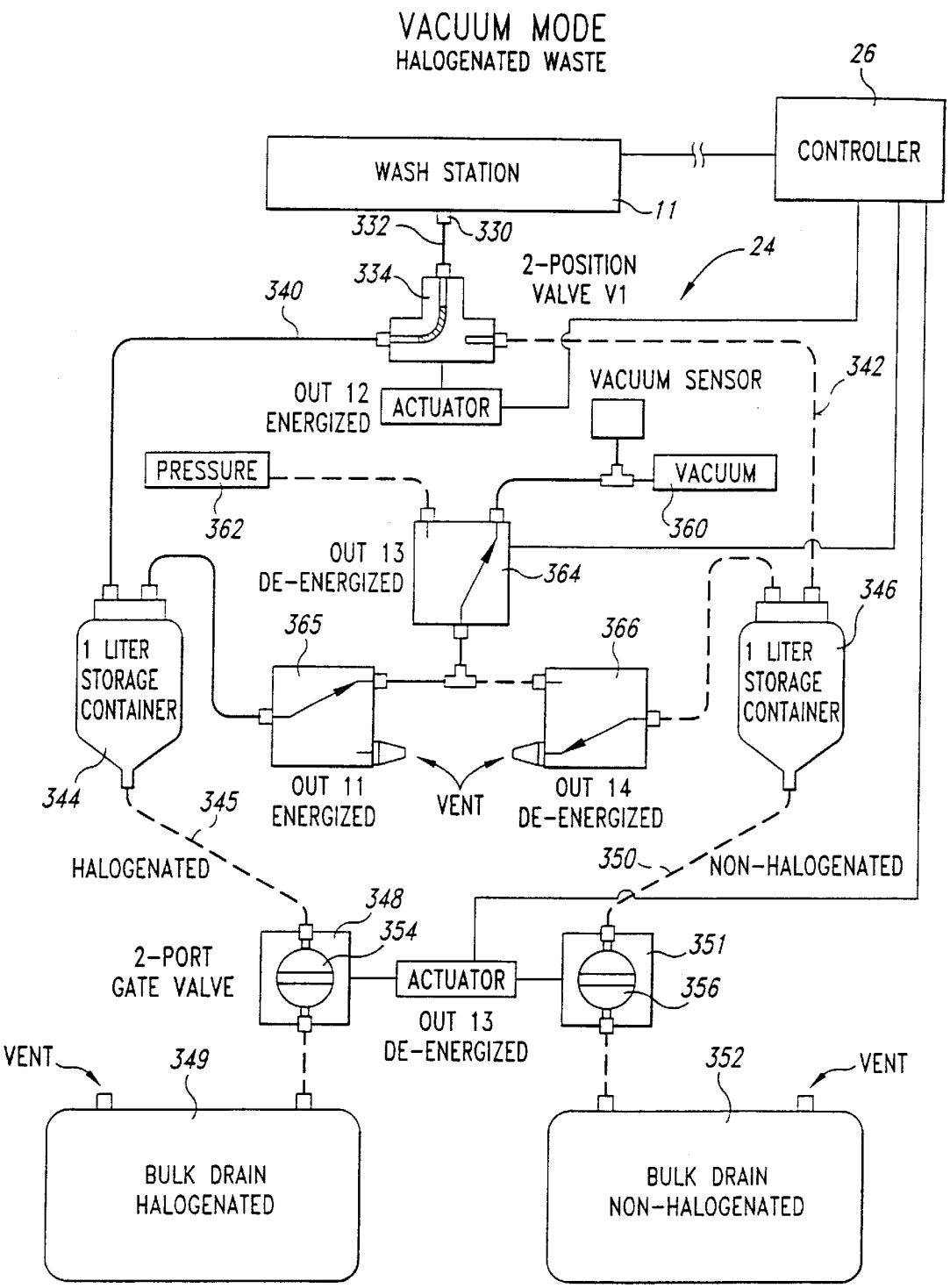
FIG. 16 is a schematic view of the waste management system of FIG. 1 shown in a vacuum mode for collecting halogenated solvent from the wash station.
Figure 17:
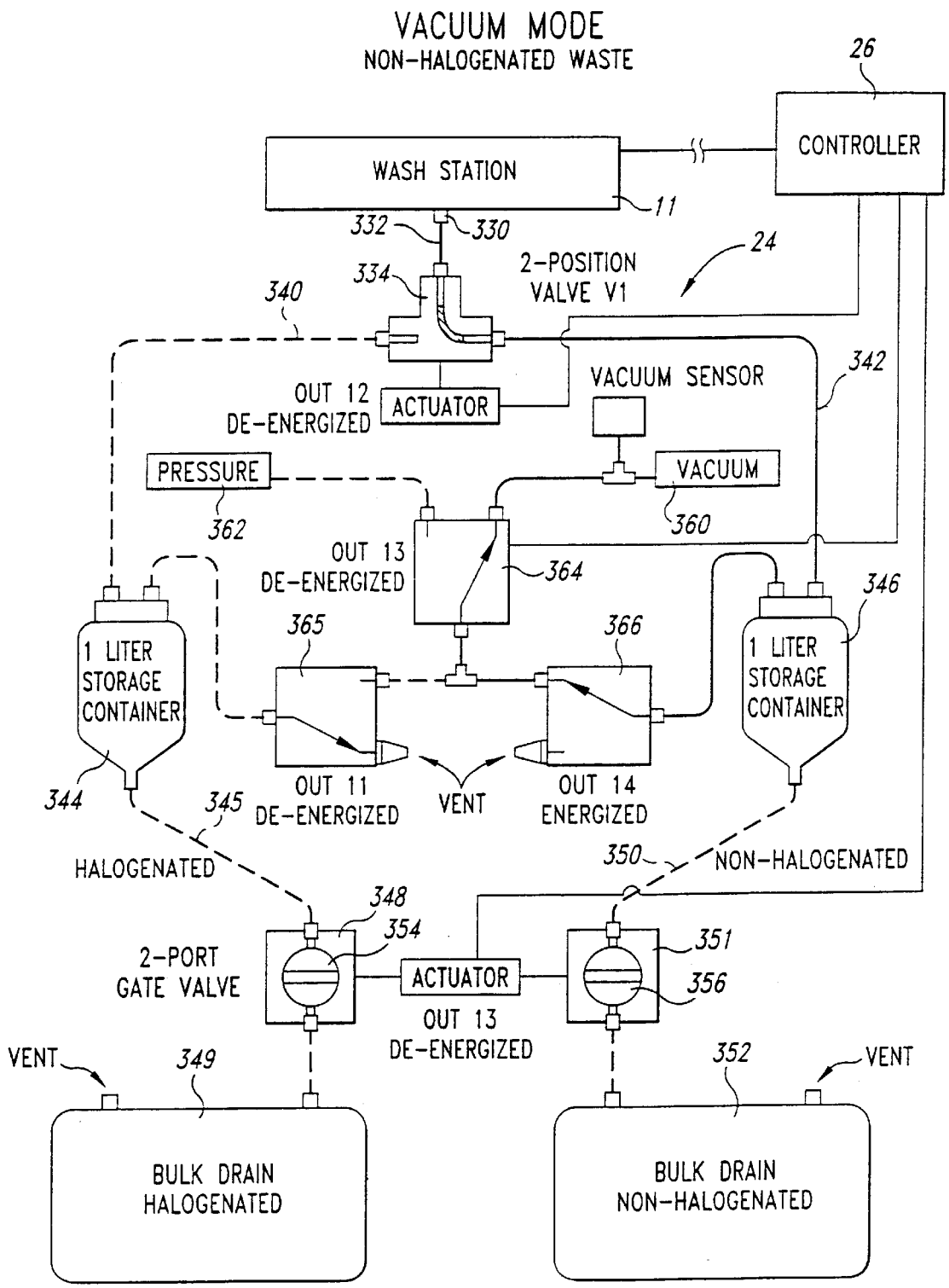
FIG. 17 is a schematic view of the waste management system of FIG. 1 shown in a vacuum mode for collecting non-halogenated solvent from the wash station.

As best seen in FIGS. 16 and 17, the waste management system 24 has a flow control valve 334 that is connected to the waste line 332 to receive the waste solvent from the wash station 11. The flow control valve 334 is connected to first and second drain lines 340 and 342. The flow control valve 334 is adjustable so the waste flow can be directed into either the first or second drain lines 340 and 342. In the exemplary embodiment, the solvent used in the wash station 11 is either a halogenated solvent or a non-halogenated solvent, and the waste management system 24 controls the solvent flow from the wash station to keep the halogenated and non-halogenated solvents separate from each other. Although the exemplary embodiments are discussed with respect to solvents, the wash station assembly 10 is usable with other fluids.

In the exemplary embodiment, the flow control valve 334 directs the halogenated solvents into the first drain line 340, and the first drain line directs the halogenated solvent into a first storage tank 344. The second drain line 342 receives the non-halogenated solvents and directs the solvents to a second storage tank 346. In one embodiment, the first and second storage tanks 344 and 346 are 1-liter temporary storage tanks for the respective waste solvent. The first storage tank 344 is connected by a drain line 345 to a first valve assembly 348 that, in turn, is connected to a first bulk storage receptacle 349 for the halogenated solvent. The first valve assembly 348 has a gate valve 354 that controls a flow of the halogenated waste solvent to the first storage receptacle 349. The second storage tank 346 is connected by a separate drain line 350 to a second valve assembly 351 that, in turn, is connected to a second bulk storage receptacle 352, for the non-halogenated solvent. The second valve assembly 351 has a gate valve 356 that controls the flow of non-halogenated solvent to the second storage receptacle 352.

Figure 18:
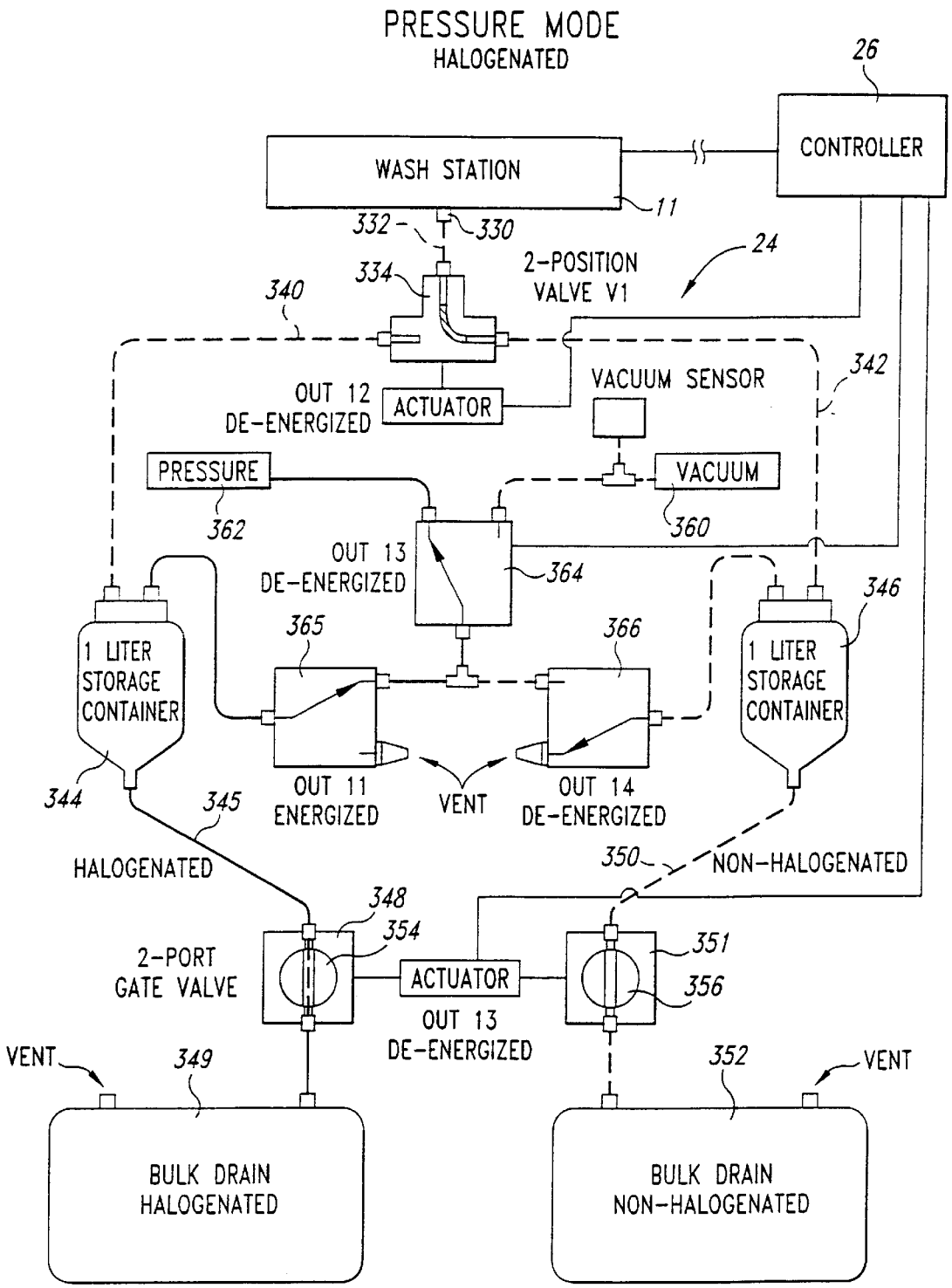
FIG. 18 is a schematic view of the waste management system of FIG. 1 shown in a pressure mode to transfer halogenated solvent from a waste storage tank to a bulk waste receptacle for halogenated solvents.

The waste management system 24 is connected to the controller 26, and the controller controls the position of the flow control valve 334 depending upon the type of solvent passing through the wash station 11. As discussed above, the controller 26 controls and monitors the position of the wash station's selector valve 46, thereby monitoring whether a halogenated or non-halogenated solvent is passed through the selector valve. When a halogenated solvent is passed through the selector valve 46, the controller 26 moves the flow control valve 334 in the waste management system to a, first position shown in FIG. 16 that directs the flow of waste solvent into the first drain line 340 and to the first storage tank 344 for the halogenated solvent. As best seen in FIG. 18, when a non-halogenated solvent is passed through the selector valve 46, the controller 26 moves the flow control valve 334 to a second position to direct the flow cf waste solvent into the second drain line 342 and to the second storage tank 346 for the non-halogenated solvent.

As best seen in FIGS. 16–20, the waste management system 24 includes a vacuum source 360 and a pressure source 362 each coupled to the first and second storage tanks 344 and 346. The vacuum/pressure control valve 364 is connected to the controller 26 and is movable to select either vacuum from the vacuum source 360 or pressure from the pressure source 362 to create a negative or positive pressure within either the first or second storage tanks 344 and 346, as controlled by control valves 365 and 366.

Figure 19:
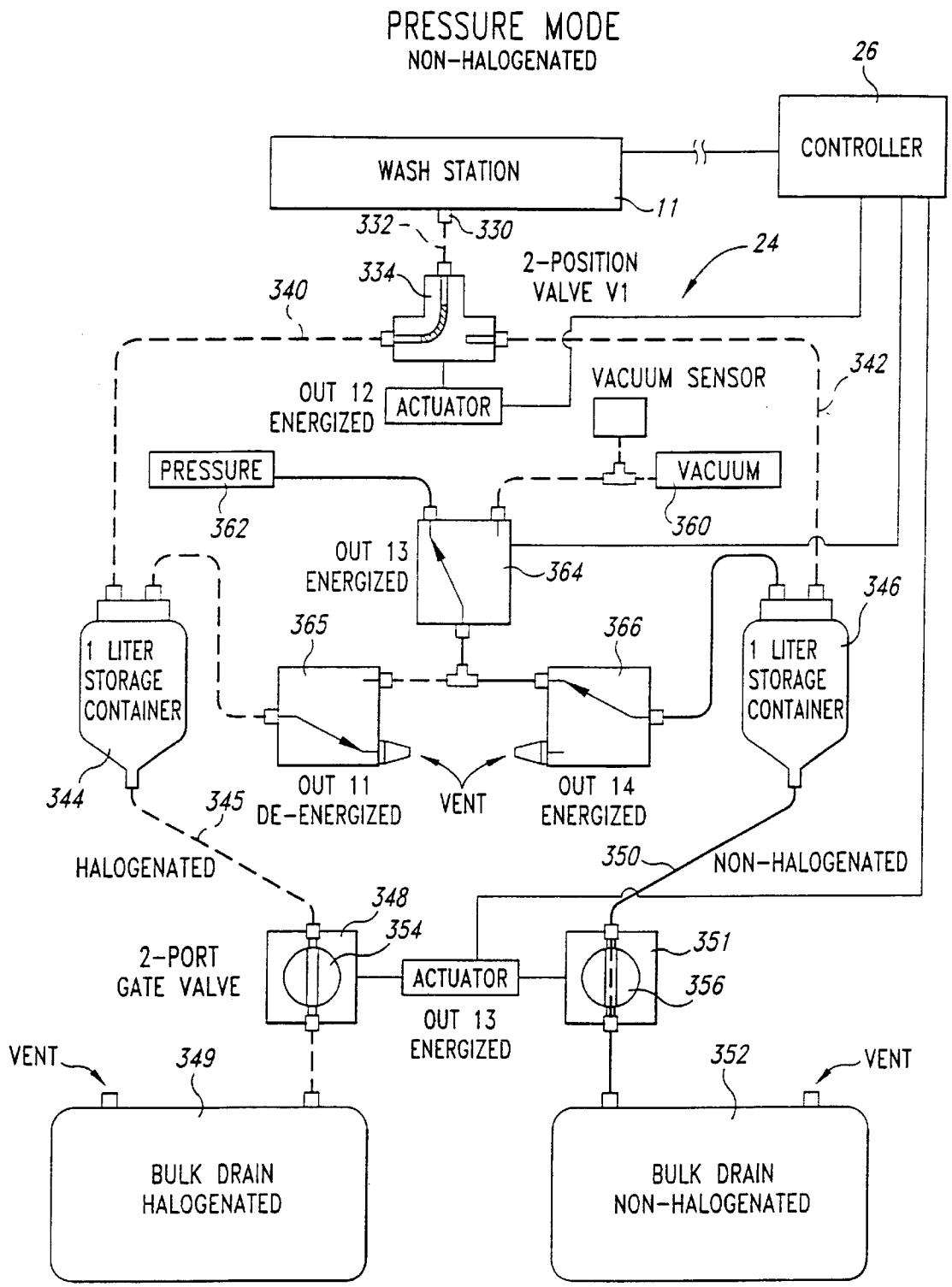
FIG. 19 is a schematic view of the waste management system of FIG. 1 in a pressure mode for directing non-halogenated solvent from a waste storage tank to a bulk waste receptacle for non-halogenated solvents.

The waste management system 24 of the exemplary embodiment includes a vacuum/pressure control valve 364 coupled to the vacuum and pressure sources 360 and 362. The vacuum/pressure control valve 364 is movable between a vacuum position, shown in FIGS. 16 and 17, and a pressure position, shown in FIGS. 18 and 19. The vacuum/pressure control valve 364 is connected by pneumatic lines to a first control valve 365, that, in turn, is connected to the first storage tank 344. The first control valve 365 is movable between a vacuum/pressure position, shown in FIGS. 16 and 18, and a vented position, shown in FIGS. 17 and 19. When the first control valve 365 is in the vacuum/pressure position and the vacuum/pressure control valve 354 is in the vacuum position, as shown in FIG. 16, a partial vacuum is applied to the first storage tank 344. When the first control valve 365 is in the vacuum/pressure position and the vacuum/pressure control valve 364 is in the pressure position as shown in FIG. 18, positive pressure is applied to the first storage tank 344. When the first control valve 365 is in the vented position, as shown in FIGS. 17 and 19, the first storage tank 344 is vented and at ambient pressure.

The vacuum/pressure control valve 364 is also connected by pneumatic lines to a second control valve 366 that, in turn, is connected to the second storage tank 346. The second control valve 366 is movable between a vacuum/pressure position, shown in FIGS. 17 and 19, and a vented position, shown in FIGS. 16 and 18. When the second control valve 366 is in the vacuum/pressure position and the vacuum/pressure control valve 364 is in the vacuum position, as shown n FIG. 17, a partial vacuum is applied to the second storage tank 346. When the second control valve 366 is in the vacuum/pressure position and the vacuum/pressure control valve 364 is in the pressure position, as shown in FIG. 19, positive pressure is applied. to the second storage tank 346. When the second control valve 366 is in the vented position, as shown in FIGS. 16 and 18, the second storage tank 346 is vented and is at ambient pressure.

As best seen in FIG. 16, when a halogenated solvent is passed through the wash station 11, the vacuum/pressure control valve 364 is in the vacuum position, the first control valve 365 is in the vacuum/pressure position, and the second control valve 366 is in the vented position, thereby creating a partial vacuum in the first storage tank 344. Accordingly, the halogenated solvent is drawn through the first drain line 340 to the first storage tank 344.

As best seen in FIG. 17, when a non-halogenated waste solvent is passed through the wash station 11, the vacuum/pressure control valve 364 is in the vacuum position, the first control valve 365 is switched to the vented position, and the second control valve 366 is switched to the vacuum/pressure position, thereby creating a partial vacuum within the second storage tank 346. Accordingly, the non-halogenated solvent is drawn through the second drain line 342 to the second storage tank 346.

As best seen in FIG. 18, when the first storage tank 344 is to be emptied into the first bulk waste receptacle 349, the flow control valve 334 is moved so solvent cannot flow from the wash station 11 into the first drain fine 340. The vacuum/pressure control valve 364 is positioned in the pressure position, the first control valve 365 is positioned in the vacuum/pressure position, and the second control valve 366 is positioned in the vented position. The pressure source 362 then provides a positive pressure to the first storage tank 344 upon. The positive pressure forces the halogenated solvent out of the first storage tank, through a drain line and through the gate valve 354 of the first valve assembly 348, which is in an open position. The halogenated solvent flows into and is contained the first waste receptacle 349.

As best seen in FIG. 19, when the second storage tank 346 is to be emptied, the flow control valve 334 is closed so solvent cannot flow from the wash station 11 into the second drain line 342. The vacuum/pressure control valve 364 is positioned in the pressure position, the first control valve 365 is positioned in the vented position, and the second control valve 366 is positioned in the vacuum/pressure position. The pressure source 362 is then activated to provide a positive pressure into the second storage tank 346. The positive pressure forces the non-halogenated solvent out of the second storage tank 346, through the gate valve 356 of the second valve assembly 351, which is in the open position, and into the second waste receptacle 352 for the non-halogenated solvent.

Figure 20:
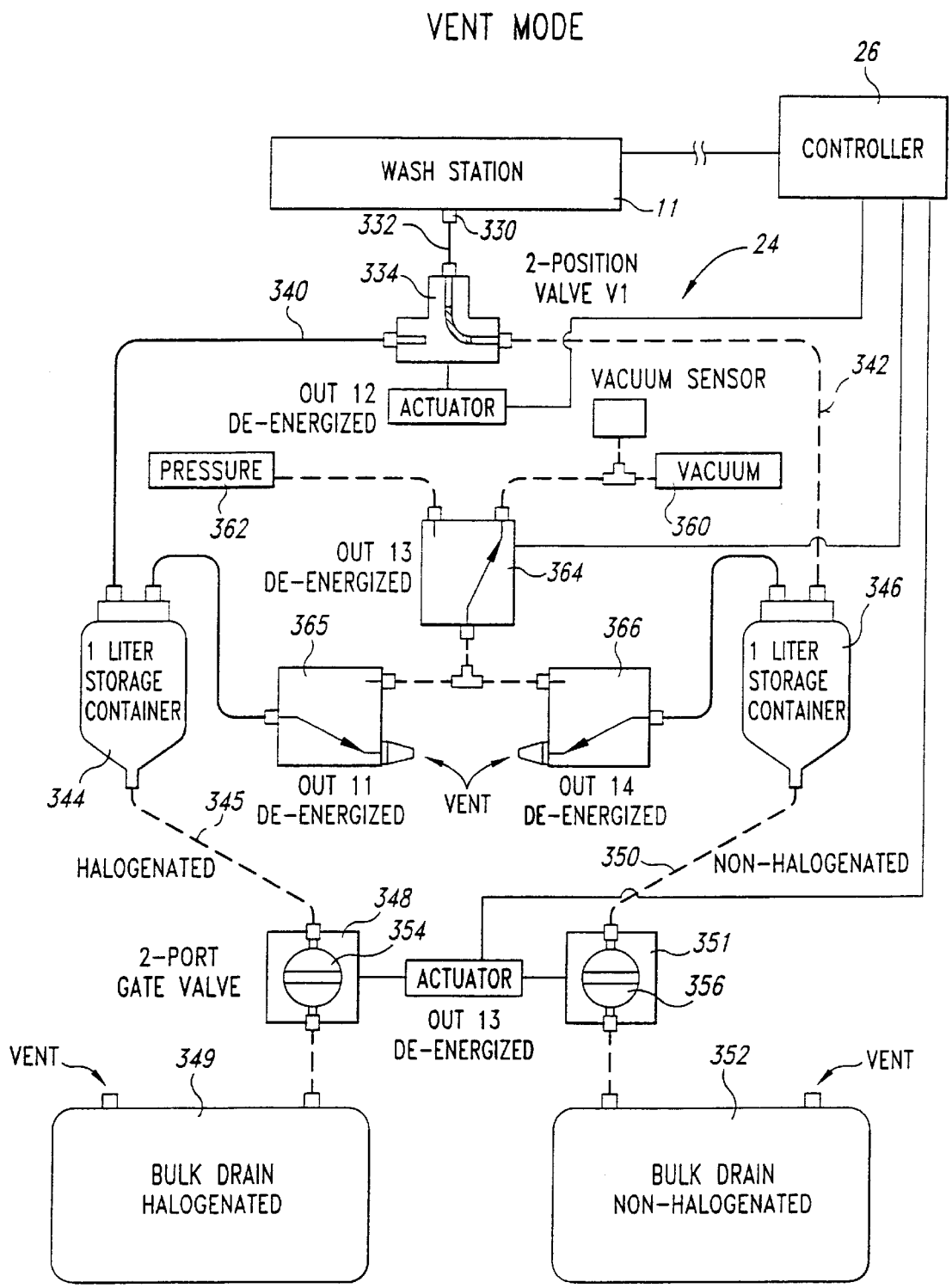
FIG. 20 is a schematic view of the waste management system of FIG. 1 in a vent mode wherein solvent within the waste management system is contained therein and the system is vented to atmosphere, for example, when the wash station is not in use.

As best seen in FIG. 20, the waste management system 24 is also configurable to a closed, vented mode wherein the first and second control valves 365 and 366 are positioned in the vented position and the gate valves 354 and 356 are closed. Accordingly, the waste management system 24 is at a vented, non-pressurized or non-vacuum state, such as when the wash station and vacuum stations are not in operation, thereby minimizing wear and tear on the waste management system when not in use.

Example of Operation

The many features of the exemplary embodiments described above facilitate the relatively quick, efficient and automated generation of chemical libraries. In the following discussion, a synthesis operation involving two selected reaction blocks is discussed, although it will be understood that the following discussion will apply for other types of synthesis operations.

In a typical operation, two reaction blocks 12 with the solid phase samples therein are positioned and secured to the docking station 13, as best seen in FIG. 1. The dispensing assembly 14 is positioned over the reaction blocks 12 in the dispensing position. The controller 26 generates start-up instructions such that the selector valve 46 is moved to a selected first position to allow a selected pressurized solvent to flow therethrough. The dispensing assembly 14 is also positioned with the syringes 42 ready to move along the aspirating stroke to receive the solvent therein. The solvent dispensing assembly's drive motor 198 and actuators 190 are activated and the syringes 42 are moved through the aspirating stroke thereby loading the syringes with a controlled amount of the selected solvent. The dispensing assembly 14 is then moved to the lowered position, as shown in FIG. 3, so the pipetting needles 32 penetrate the septum of the reaction blocks 12 and are positioned in the reaction chambers 38. The syringes 42 are then moved through the dispensing stroke to force the solvent out of the syringes into the reaction chambers 38. The dispensing assembly 14 is then moved upwardly from the lowered position to the raised position. Simultaneously, the syringes 42 are moved through the aspirating stroke to reload the syringes with the selected solvent.

After a selected period of time during which the solvents may be vortexed by activating the vortexing shaker, the solvent is drained from the reaction blocks 12 to the waste management system 24 to the appropriate halogenated or non-halogenated solvent storage tank 344 or 346. After the reaction blocks 12 have been drained, the solvent dispensing, vortexing and draining cycle is repeated, for example, three times to provide a sufficient degree of washing of the samples within the reaction blocks.

After the last dispensing cycle, the dispensing assembly 14 is moved to the raised position, but the syringes 42 remain in the dispensed position, so additional solvent is not drawn into the syringes. The dispensing assembly 14 is then moved laterally and positioned over the rinse tubes 22, and the dispensing assembly is moved to the lowered position, so the pipetting needles 32 extend into the rinse tubes 22. A rinse solvent from one of the tanks 16 is aspirated into and dispensed through the needles into the rinse tube, thereby rinsing the needles inside and out.

When the dispensing assembly 14 is positioned over the rinse tubes 22, the pair of reaction blocks 12 can be exchanged for the next set of reaction blocks to be washed. The dispensing assembly 14 is then moved to the raised position and moved laterally to the position over the reaction blocks 12. As the dispensing assembly 14 is moving laterally, the syringes 42 are simultaneously moved through the aspirating stroke so as to load the syringes with the same or another one of the solvents. The wash station 11 is then ready for another washing cycle.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A wash station for washing a selected sample in a sample containing assembly, the wash station being connectable to a fluid line connected to a fluid source, comprising:

a frame;

a distribution manifold connected to the fame, the distribution manifold having a manifold inlet positioned to receive fluid from the fluid line, the distribution manifold having a plurality of distribution channels in fluid connection to the manifold inlet, the distribution channels each having a flow control valve therein to allow fluid to flow in only one direction in the respective distribution channel, and each distribution channel having a separate channel outlet; and an array of fluid dispensers connected to the distribution manifold, each fluid dispenser being connected to the channel outlet of a respective distribution channel to receive the fluid passing through the distribution channel, the fluid dispenser being adapted to dispense the fluid therefrom, and each flow control valve in the respective distribution channel is movable between an open position to allow the fluid to flow into the respective fluid dispenser and a closed position to block flow of the fluid in the distribution channel away from the respective fluid dispenser.

2. The wash station of claim 1 further including a gate valve connected to the distribution manifold and positioned to control fluid flow from the fluid source to the distribution source.

3. The wash station of claim 1 having a plurality of fluid lines and a plurality of fluid sources with fluids therein, the assembly further comprising a selector valve connectable to the fluid lines, the selector valve being adjustable to one of a plurality of positions to allow a selected one of the fluids to pass therethrough to the distribution manifold.

4. The wash station of claim 3 wherein the selector valve includes a body with a plurality of fluid inlets connectable to the fluid lines, a plurality of fluid passageways in the body communicating with the fluid inlets, a valve member connected to the body, and an outlet channel communicating with the valve member and the manifold inlet, the valve member having a valve channel therethrough that communicates with the outlet passageway, the valve member being adjustable to position the valve channel in communication with one of the fluid passageways to direct fluid from the one of the fluid passageways into the outlet passageway and into the manifold inlet and the valve member blocks the other fluid passageways to prevent fluid from flowing therethrough.

5. The wash station of claim 3 wherein the selector valve assembly has a gate valve in the outlet passageway, the gate valve being adjustable between open and closed positions to control the flow of fluid through the outlet passageway.

6. The wash station of claim 5 wherein the selector valve includes a valve control assembly that is connected to the valve member and that is adjustable to move the valve member to align the valve channel with the selected one of the fluid passageways.

7. The wash station of claim 3, further comprising a programmable controller coupled to the selector valve for controlling which fluid flows through the selector valve to the fluid passageways.

8. The wash station of claim 1 wherein the fluid dispensers are syringes.

9. The wash station of claim 1 wherein the distribution manifold and the fluid dispensers are movable as a unit vertically and laterally relative to the frame.

10. The wash station of claim 1 further comprising a plurality of distributor members connect to the fluid dispense, each distributor member having an interior passageway, and a radially directed aperture in a distal end portion, the aperture communicating with the interior passageway to direct a flow of fluid radially away from the distal end portion.

11. The wash station of claim 1, further including a distributor support connected to the frame and the distribution manifold, and a drive mechanism connected to the distributor support, the distributor support and distribution manifold being movable as a unit by the drive mechanism relative to the frame.

12. The wash station of claim 11 further including an upper support member spaced apart from the distribution manifold, and a second drive mechanism interconnecting distribution manifold and the upper support member, the fluid dispensers extending between the distribution manifold and the upper support member, and the upper support member being movable by a second drive mechanism relative to the distribution manifold between first and second positions, the fluid dispensers being compressed and moved along a discharge stroke as the upper support member moves from the second position toward the first position, and the fluid dispensers are extended and moved along an aspirating stroke as the upper support member moves from the second position toward the first position.

13. The wash station of claim 1, further including an upper support member spaced apart from the distribution manifold with the fluid dispensers movably extending between the distribution manifold and the upper support member, and a drive mechanism interconnecting the distribution manifold and the upper support member, the upper support member being movable by the drive mechanism relative to the distribution manifold between first and second positions, and the fluid dispensers each include a connector connected to the distribution manifold, a barrel attached to the connector and sized to receive the fluid from the distribution manifold, and a plunger with one end slidably positioned in the barrel and another end attached to the upper support member, the plunger moving axially within the barrel as the upper support member moves between the first and second positions.

14. The wash station of claim 13 wherein the connector has an outlet port and an inlet port, the inlet port connecting the barrel with the respective distribution channel of the distribution manifold, the plunger moves within the barrel away from the distribution manifold along an aspirating stroke to draw the fluid through the inlet port and into the barrel as the upper support member moves from the first position to the second position, and the plunger moves toward the distribution manifold along a dispensing stroke to dispense fluid through the outlet port into the distributor member.

15. The wash station of claim 14 wherein the connector has a valve in communication with the outlet port and positioned to prevent fluid or air from entering the barrel through the outlet port.

\* \* \* \* \*